US007212933B2

(12) United States Patent
Kouri et al.

(10) Patent No.: US 7,212,933 B2
(45) Date of Patent: May 1, 2007

(54) ABSOLUTELY AND UNIFORMLY CONVERGENT ITERATIVE APPROACH TO INVERSE SCATTERING WITH AN INFINITE RADIUS OF CONVERGENCE

(75) Inventors: Donald J. Kouri, Houston, TX (US); Amrendra Vijay, Houston, TX (US); Haiyan Zhang, Houston, TX (US); Jingfeng Zhang, Houston, TX (US); David K. Hoffman, Ames, IA (US)

(73) Assignee: The University of Houston System, Houston, TX (US)

( * ) Notice: Subject to any disclaimer, the term of this patent is extended or adjusted under 35 U.S.C. 154(b) by 0 days.

(21) Appl. No.: 10/806,045

(22) Filed: Mar. 22, 2004

(65) Prior Publication Data

US 2005/0021266 A1 Jan. 27, 2005

Related U.S. Application Data

(60) Provisional application No. 60/456,175, filed on Mar. 20, 2003.

(51) Int. Cl.
*G01R 23/16* (2006.01)

(52) U.S. Cl. ............................ 702/76; 702/1; 702/66; 702/67; 702/127; 702/134; 356/446; 356/625

(58) Field of Classification Search .................. 702/76, 702/1, 66, 67, 127, 134; 356/446, 625
See application file for complete search history.

(56) References Cited

U.S. PATENT DOCUMENTS 6,867,866 B1 * 3/2005 Chang et al. ............... 356/446

OTHER PUBLICATIONS

H. Abdullah and A K Louis "The approximate inverse for solving an inverse scattering problem for acoustic waves in an inhomogeneous medium", 1999 IOP Publishing Ltd.*

* cited by examiner

*Primary Examiner*—Marc S. Hoff
*Assistant Examiner*—Phuong Huynh
(74) *Attorney, Agent, or Firm*—Robert W. Strozier

(57) ABSTRACT

A method and system for solving the inverse acoustic scattering problem using an iterative approach with consideration of half-off-shell transition matrix elements (near-field) information, where the Volterra inverse series correctly predicts the first two moments of the interaction, while the Fredholm inverse series is correct only for the first moment and that the Volterra approach provides a method for exactly obtaining interactions which can be written as a sum of delta functions.

12 Claims, 1 Drawing Sheet

US 7,212,933 B2

ABSOLUTELY AND UNIFORMLY CONVERGENT ITERATIVE APPROACH TO INVERSE SCATTERING WITH AN INFINITE RADIUS OF CONVERGENCE

RELATED APPLICATIONS

This application claims provisional priority of U.S. Provisional Patent Application Ser. No. 60/456,175 filed 20 Mar. 2003.

ACKNOWLEDGMENT OF GOVERNMENTAL SPONSORSHIP

Portions of the research that supports the subject matter of this application was supported by a grant from the National Science Foundation grant number CHE-0074311 and U.S. Department of Energy Grant No. 2-7405-ENG82.

BACKGROUND OF THE INVENTION

1. Field of the Invention

The present invention relates to a method for analyzing spectra including contributions from scattering so-called inverse scattering analysis using a renormalized form of the Lippmann-Schwinger equations, and to a system implemented on a computer and attached to an analytical instrument where a spectrum of interest is received by the instrument and analyzed in the computer using the renormalized form of the Lippman-Schwinger equations of this invention.

More particularly, the present invention relates to a method for analyzing spectra including contributions from scattering so-called inverse scattering analysis using a renormalized form of the Lippmann-Schwinger equations, where the renormalized equation permits absolute and uniform convergence of the equation regardless of the strength of interaction in the system from which the spectrum was obtained, and to a system implemented on a computer and attached to an analytical instrument where a spectrum of interest is received by the instrument and analyzed in the computer using the renormalized form of the Lippman-Schwinger equations of this invention.

2. Description of the Related Art

Many spectral characterization include inverse scattering components resulting from internal reflections of an incident waveform. These inverse scattering components can give information on both near field and far field properties of the object being analyzed. However, traditional application of the Lippmann-Schwinger equations to analyzed spectra including inverse scattering components are less the satisfactory because the Lippmann-Schwinger equations often do not converge or give oscillatory solutions that must be truncated to product approximate and sometimes misleading analyses.

Thus, there is a need in the art for an improved mathematical theory for analyzing inverse scattering components that always permits solutions because the equations absolutely and uniformly converge.

SUMMARY OF THE INVENTION

The present invention provides a method for analyzing inverse scattering components of a spectrum of an object of interest, where the method utilizes equations that are absolutely and uniformly convergence and amenable efficient iterative computational determination, with leading terms allowing for fast tentative identification of the object from which the spectrum is obtained.

The present invention also provides a method for analyzing inverse scattering components of a spectrum of an object of interest, where the method utilizes equations that are absolutely and uniformly convergence and amenable efficient iterative computational determination, with leading terms allowing for fast tentative identification of the object from which the spectrum is obtained, where the method involves obtaining a reflectance and/or transmission spectra of an object of interest using an incident waveform (electromagnetic or sonic). The spectra is then analyzed using the inverse scattering equations of this invention implemented on or in a processing unit (digital or analog) to derive a potential function representing the object. Generally, an adequate potential function can be derived from the first few leading terms of the iterative solution of the equations, where few means the first four terms, preferably the first three terms and particularly the first two terms.

The present invention also provides an analytical instrument including an excitation source for producing an incident waveform, a detector for receiving either a transmission spectrum or a reflectance spectrum or both a transmission spectrum and a reflectance spectrum of an object or volume of interest, and a processing unit for analyzing the spectra, where the processing unit includes software encoding the inverse scattering method of this invention.

The present invention also provides a sonic analytical instrument including a sonic excitation source for producing an incident sonic waveform, a detector for receiving either a sonic transmission spectrum or a sonic reflectance spectrum or both a sonic transmission spectrum and a sonic reflectance spectrum of an object or volume of interest, and a processing unit for analyzing the sonic spectra, where the processing unit includes software encoding the inverse scattering method of this invention.

The present invention also provides an electromagnetic analytical instrument including an electromagnetic excitation source for producing an incident electromagnetic waveform, a detector for receiving either an electromagnetic transmission spectrum or an electromagnetic reflectance spectrum or both an electromagnetic transmission spectrum and an electromagnetic reflectance spectrum of an object or volume of interest, and a processing unit for analyzing the electromagnetic spectra, where the processing unit includes software encoding the inverse scattering method of this invention. Of course, the analytical instrument can include both sonic and electromagnetic excitation sources and detectors.

BRIEF DESCRIPTION OF THE DRAWINGS

The invention can be better understood with reference to the followina detailed description together with the appended illustrative drawings in which like elements are numbered the same.

Figure 1A:
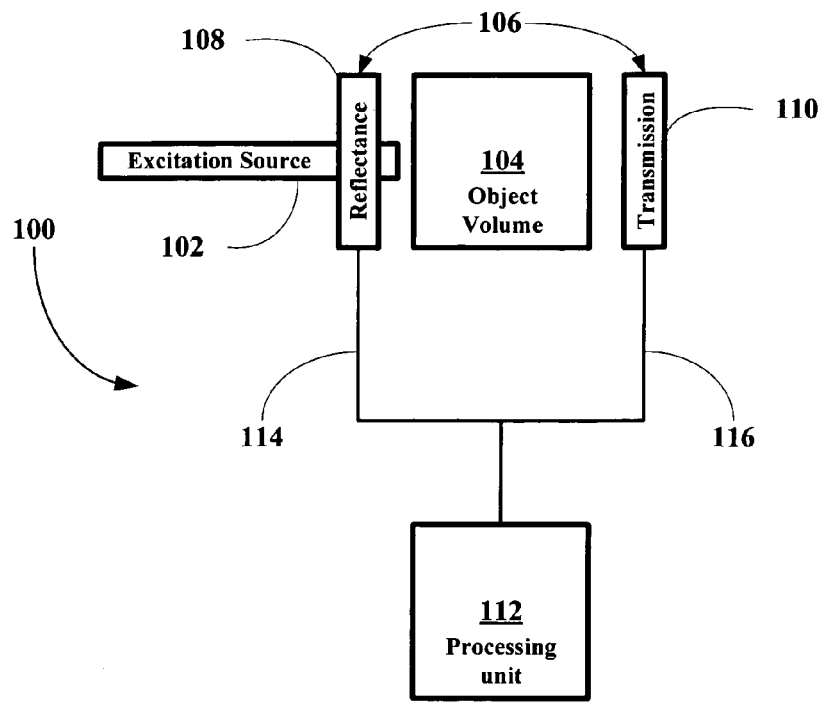
FIG. 1A depicts an embodiment of an analytical instrument of this invention.

Referring now of FIG. 1A, an embodiment of an analytical instrument of this invention, generally 100, is shown to include an excitation source 102 adapted to produce an incident waveform such as a sonic waveform or an electromagnetic waveform which is directed into an object or volume 104 to be analyzed. The instrument 100 also includes a detector 106 having a reflectance detection component 108 and a transmission detection component 110, where the reflectance detection component 108 is adanted to detect a reflectance spectrum and the transmission detection component 110 is adapted to detect a transmission spectrum. The detector components 108 and 110 are connected to a processing unit 112 via wires 114 and 116, where the processing unit 112 includes software encoding the methods of this invention.

Figure 1B:
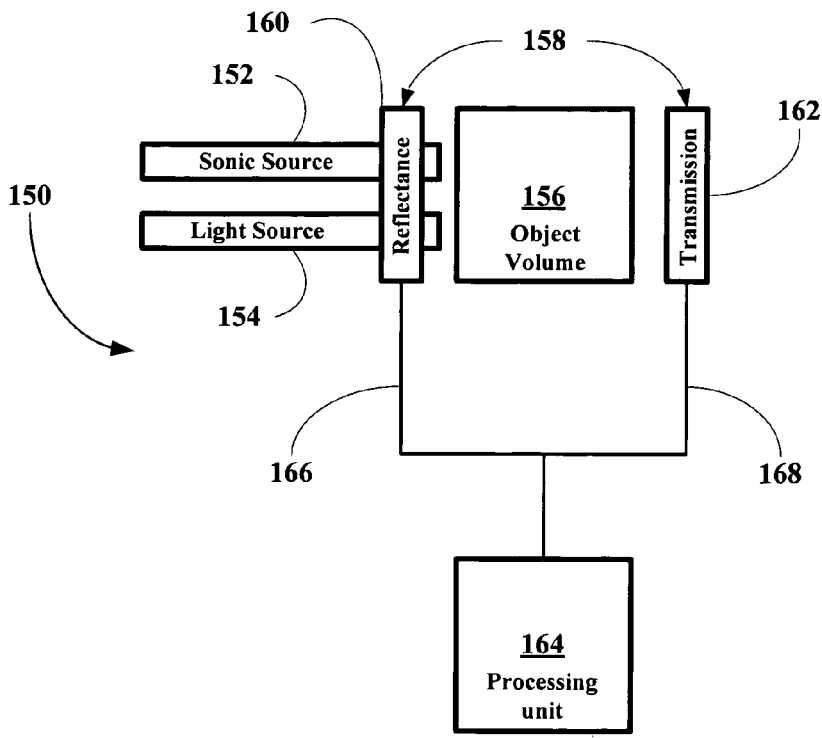
FIG. 1B depicts another embodiment of an analytical instrument of this invention.

Referring now of FIG. 1B, another embodiment of an analytical instrument of this invention, generally 150, is shown to include an sonic excitation source 152 adapted to produce an incident sonic waveform and an electromaanetic excitation source 154 adapted to produce an incident electromagnetic waveform, which are directed into an object or volume 156 to be analyzed. The instrument 150 also includes a detector 158 having a reflectance detection component 160 and a transmission detection component 162, where the reflectance detection component 160 is adapted to detect a reflectance spectrum and the transmission detection component 162 is adapted to detect a transmission spectrum. The detector components 160 and 162 are connected to a processing unit 164 via wires 166 and 168, where the processing unit 164 includes software encoding the methods of this invention.

We present a new inverse scattering series for quantum elastic scattering in three spherical dimensions. The new series, which converges absolutely, independent of the strength of the scattering interaction, results from a renormalization transformation of the Lippmann-Schwinger Fredholm integral equation to a Volterra form. A new feature of the formulation is that it does not require determination of phase shifts, and it can be applied even to integral cross section measurements. The approach is illustrated by application to a simple example problem.

DETAILED DESCRIPTION OF THE INVENTION

The inventor has found that the inverse scattering problem encountered in many field of spectroscopy can be solved in a more rigorous manner by applying a simple but effective renormalization condition on the traditional Lippmann-Schwinger equation. The simple and effective remomalization of the Lippmann-Schwinger equation results in a set of equations that are absolutely and uniformly convergent for all systems regardless of the strength of the interactions between the probing waveform and the object being probed obviating the convergence problems that plague traditional Lippmann-Schwinger analyses. In fact, the inventors have found that calculation of only a limited number of terms provides an accurate enough representation of the object being probed, either near or far field, for rapid identification. The renormalized equations find application in all electromagnetic and sonic spectrometry application and is especially well-suited for analysis of data from very low frequency electromagnetic imaging used to tract undersea objects such as submarines.

In this application, we introduce an approach to the inverse scattering series that completely solves the problem of convergence[7A]. This is achieved by renormalizing the Lippmann-Schwinger equation from a Fredhohm to a Volterra structure. It was proved that the resulting inverse Born series converges absolutely and uniformly independent of the strength of the interaction. However, the issue of how best to deal with the need for half-o-shell scattering information remains outstanding. We base our strategy for solving the inverse problem on exploiting the superior convergence properties of the Volterra-based inverse series in combination with the introduction of a parameterization of the interaction that allows for a greatly simplified determination of the interaction parameters. This enables us to take account of half-o-shell (near field) effects.

Inverse Scattering Theory: Strategies Based on the Volterra Inverse Series for Acoustic Scattering I. Introduction It is also important to note, and we emphasize the fact, that use of a Volterra-based inversion requires either a) measurement of both the reflection and transmission amplitudes in order to achieve the simplest form of inversion b) the solution of more complicated, nonlinear algebraic equations if only the reflection amplitude is measured. In Section II of this application, we present a simple analysis that shows clearly the need to deal with half-o-shell or near-field effects in order to treat the problem. In Section III, we present a general analysis of the moments of the Fredholm and Volterra Born approximations compared to the moments of the true interaction. This shows that the Volterra-based Born expansion yields one higher moment before the half-off-shell effects come into play. Then in Section IV, we consider inversion of the scattering produced by any interaction that can be expressed as a sum of Dirac delta functions (a model interaction that is shown in more detail in Appendix B to be of practical utility). This interaction also nicely illustrates the convergence properties of the Volterra series. For simplicity, we restrict ourselves to a scalar scattering wave (i.e., acoustic scattering), but the analysis is valid also for more complicated electromagnetic scattering. In Section V, we discuss the data required for implementation of the Volterra-based inversion. Finally, in Section VI, we give our conclusions.

II. Analysis of the Role of Half-Off-Shell Transition Amplitudes

The Born-type inverse scattering series is most simply obtained from the abstract Lippmann-Schwinger equation $$T_k = V + VG_{0k}^+ T_k \quad (1)$$

where V is the (local) interaction, $T_k$ is the transition operator, and $$G_0^+$$

is the free (unperturbed) causal Green's operator, $$G_{0k}^+ = \frac{k^2}{k^2 - H_0 + i\varepsilon} \quad (2)$$

modified for the acoustic (and electromagnetic) case by the multiplicative factor, $k^2$. This factor arises because, unlike for the quantum scattering case, the scattering interaction is of the form $k^2 V$ This extra factor, $k^2$, causes important changes in the scattering behavior compared to the quantal case as is elaborated in the Appendix A. Here $k^2$ is essentially the square of the spatial wavenumber parameter, $H_0$ describes the unperturbed wave propagation. Also, we explicitly indicate that the abstract operators $T_k$ and $$G_0^+$$

depend on k as a parameter. The scattering amplitude for the process k→k' then is given (using Dirac notation for compactness)

$$\langle k'|T_k|k\rangle = \langle k'|V|k\rangle + \langle k'|VG_{0k}^+T_k|k\rangle \quad (3)$$

Taking advantage of the local character of V, we then have that $$\langle k'|T_k|k\rangle = \frac{1}{2\pi}\int_{-\infty}^{+\infty} dz e^{i(k-k')z}V(z) \quad (4)$$

It is important to note that the matrix element <k'|V|k> of the true local inter-action only depends on the difference (k−k'). Conversely, if <k'|V|k> is only a function of (k−k') then V is local. If V(z) is real, then we also have that $$\langle k'|V|k\rangle = \langle k|V|k'\rangle^* \quad (5)$$

It can then be established that <k'|V|k> and <k'|V|k'> cannot simultaneously depend only on the difference (k−k) for if that were the case, then Equation (1) could be written as $$\langle k'|T_k|k\rangle = \langle k'|V|k\rangle + \int dk'' \tilde{V}(k''-k')\langle k''|G_{0k}^+|k''\rangle \tilde{T}_k(k-k'') \quad (6)$$
$$= \langle k'|V|k\rangle + \int dy \tilde{V}(k-k'-y)\langle k''|G_{0k}^+|k''\rangle \tilde{T}_k(y)$$
$$= \langle k'|V|k\rangle + \int dy \tilde{V}(k-k'-y')\frac{k^2}{(2k-y)y+i\varepsilon}\tilde{T}_k(y)$$

The last line, which results from substitution of the Green's function of Equation (2) into the previous line, clearly shows that the integral, and hence the LHS of this equation, is not solely a function of k−k', which is a contradiction. For inversion, we write Equation (1) as an equation for <k'|V|k>

$$\langle k'|V|k\rangle = \langle k'|T_k|k\rangle - \langle k|VG_{0k}^+T_k|k\rangle \quad (7)$$

Using the resolution of the identity $$1 = \int dk''|k''\rangle\langle k''| \quad (8)$$

this equation becomes $$\langle k'|V|k\rangle = \langle k'|T_k|k\rangle - \int dk'' \frac{\langle k'|V|k''\rangle\langle k''|T_k|k\rangle}{k^2-k''^2+i\varepsilon} \quad (9)$$

which is an exact equation. We first observe that if we take |k'|=|k| so that <k'|T_k|k> corresponds to an on-shell matrix element, then <k'|V|k"> still involves both on-shell and half-on-shell T matrix elements.

As we have seen, although V is taken to be a local operator, it cannot be true in general that $T_k$ is local (or, more precisely, <k'|T_k|k> is not solely a function of k−k'). The approach of Moses, Razavy, and Prosser [3A–5A] involves additional expansions of (k'Vk) and (k'T_k k) in a power series of the on-shell (reflection) amplitude. Thus, in addition to the issue of convergence of the Born expansion of Equation (1), there is also the question of convergence of these expansions solely in terms of the far field reflection amplitude. We note that this analysis also applies to the Volterra inverse integral equation. One can, in general, write the Volterra Green's operator, $\tilde{G}_{0k}$, as $$\tilde{G}_{0k}^+$$

plus a solution of the homogeneous free Green's function [7A, 8A] equation Such homogeneous solutions can always be written as a sum of separable, totally on-shell operators having the form $$O_k = \sum_n |\phi_{nk}\rangle\langle\chi_{nk}| \quad (10)$$

where $$(k^2-H_0)|\phi_{nk}\rangle = (k^2-H_0)|\chi_{nk}\rangle = 0 \quad (11)$$

Then, $$G_{0k}^+ = \tilde{G}_{0k} + O_k \quad (12)$$

(12)
and, $$T_k = V + V\tilde{G}_{0k}T_k + VO_kT_k = V[1+O_kT_k] + V\tilde{G}_{0k}T_k \quad (13)$$

We define $\tilde{T}_k$ by $$\tilde{T}_k = V + V\tilde{G}_{0k}\tilde{T}_k \quad (14)$$

where, $$T_k = \tilde{T}_k(1+O_kT_k) \quad (15)$$

Again one can show that $\tilde{T}_k$ is, in general, non-local, and a parallel analysis to that for $T_k$ holds. The major distinction between using Equation (3) to generate an inverse series for <k'|V|k> and using similar matrix elements of Equation (14), expressed as $$V = \tilde{T}_k - V\tilde{G}_{0k}\tilde{T}_k \quad (16)$$

is that the iterative solution of Equation (14) for V is guaranteed to converge absolutely and uniformly no matter how strong V is [7A, 8A]. There remains the question of whether the general matrix elements of V and $T_k$ can be expanded in convergent series of far-field amplitudes. Thus, whether one bases an inversion on $T_k$ or $\tilde{T}_k$, both require the equivalent of half-on-shell information for their implementation. We next examine the behavior of these two inversion alternatives with regard to their relations to moments of the true interaction, because this shows an important distinction in how far-field quantities affect these two.

III. Analysis of Moments of the Interaction

The moments of the interaction are defined as, $$V[n] \equiv \int_{-\infty}^{+\infty} dz\, z^n V(z) \tag{17}$$

It is clear from equations (7) and (16) that V(n) is exactly given by $$V[n] = \int_{-\infty}^{+\infty} dz\, z^n \int_{-\infty}^{+\infty} dk\, e^{-2ikz} \langle -k|V|k\rangle \tag{18}$$

leading to $$V[n] = \int_{-\infty}^{+\infty} dz\, z^n \int_{-\infty}^{+\infty} dk\, e^{-2ikz}[\langle -k|T_k|k\rangle - \langle -k|VG_{0k}^+ T_k|k\rangle] \tag{19}$$

or $$V[n] = \int_{-\infty}^{+\infty} dz\, z^n \int_{-\infty}^{+\infty} dk\, e^{-2ikz}[\langle -k|\tilde{T}_k|k\rangle - \langle -k|V\tilde{G}_{0k}\tilde{T}_k|k\rangle] \tag{20}$$

It is generally assumed that $\langle -k|T_k|k\rangle$ and $\langle -k|\tilde{T}_k|k\rangle$ are obtained experimentally by a far-field measurement. The terms involving $$\langle -k|VG_{0k}^+ T_k|k\rangle$$

and the analogous matrix element of $T_k$ are the source of far-field effects in the above equations. Again, defining, $$V_1(z) \equiv \int_{-\infty}^{+\infty} dk\, e^{-2ikz}\langle -k|T_k|k\rangle \tag{21}$$

and, $$\tilde{V}_1(z) \equiv \int_{-\infty}^{-\infty} dk\, e^{-2ikz}\langle -k|\tilde{T}_k|k\rangle \tag{22}$$

we have, $$V[n] = V_1[n] - \int_{-\infty}^{+\infty} dz\, z^n \int_{-\infty}^{+\infty} dk\, e^{-2ikz}\langle -k|VG_{0k}^+ T_k|k\rangle \tag{23}$$

and, $$V[n] = \tilde{V}_1[n] - \int_{-\infty}^{-\infty} dz\, z^n \int_{-\infty}^{+\infty} dk\, e^{-2ikz}\langle -k|V\tilde{G}_{0k}\tilde{T}_k|k\rangle \tag{24}$$

We shall now prove that, in general, $\tilde{V}_1[n]$ is exact (i.e., $\tilde{V}[n]=\tilde{V}_1[n]$ through n =1 while $V_1[n]$ is only correct for n=0. To do this, we substitute into these equations the coordinate representation matrix elements of $$G_{0k}^+$$

and $\tilde{G}_{0k}$, which are given respectively by [8A]

$$G_{0k}^+(z|z') = \frac{-ik}{2}e^{ik|z'-z|} \tag{25}$$

and $$\tilde{G}_{0k}(z|z')=k\sin(k[z'-z])H(z'-z) \tag{26}$$

Here H(z'-z) is the Heaviside function, $$H(z) = \begin{cases} 1, & z > 0 \\ 0, & z \le 0 \end{cases} \tag{27}$$

After judicious insertion of identity resolutions, we then obtain the results $$V[n] = \tag{28}$$
$$V_1[n] - \frac{i}{2}\int_{\infty}^{+\infty} dz\, z^n \int_{\infty}^{+\infty} dk \int_{\infty}^{+\infty} dz' \int_{\infty}^{+\infty} dz''\, e^{-2ikz} e^{ikz'}$$
$$V(z')k e^{ik|z'-z''|}\langle z''|T_k|k\rangle$$

and $$V[n] = \tag{29}$$
$$\tilde{V}_1[n] - \int_{\infty}^{+\infty} dz\, z^n \int_{\infty}^{+\infty} dk \int_{\infty}^{+\infty} dz' \int_{\infty}^{+\infty} dz''\, e^{-2ikz} e^{ikz'}$$
$$V(z')k\sin(k[z''-z'])H(z''-z')\langle z''|\tilde{T}_k|k\rangle$$

Next we interchange the order of the dz and dk integrals and note that $$\int_{\infty}^{+\infty} dz\, z^n e^{-2ikz} = \left(\frac{i}{2}\right)^n \frac{\partial^n}{\partial k^n}\int_{\infty}^{+\infty} dz\, e^{-2ikz} = 2\pi\left(\frac{i}{2}\right)^n \frac{\partial^n}{\partial k^n}\delta(2k) \tag{30}$$

Consequently, Equations (28) and (29) become $$V[n] = V_1[n] + \frac{\pi i^n}{2^{n-1}}\int_{\infty}^{+\infty} dz' \tag{31}$$
$$\int_{\infty}^{+\infty} dz''\, V(z')\frac{\partial^n}{\partial k^n}\left\{e^{ikz'}k e^{ik|z'-z''|}\langle z''|T_k|k\rangle\right\}_{k=0}$$

and $$V[n] = \tilde{V}_1[n] + \frac{\pi i^{n+1}}{2^n}\int_{\infty}^{+\infty} dz' \int_{\infty}^{+\infty} dz''\, V(z')H(z''-z') \tag{32}$$
$$\frac{\partial^n}{\partial k^n}\left\{e^{ikz'}k\sin[k(z''-z')]\langle z''|\tilde{T}_k|k\rangle\right\}_{k=0}$$

Now the essential point to note is that when n=0 the second terms in both Equations (31) and (32) vanish since there is no derivative and k=0. Therefore, we conclude that $$V[0]=V_1[0]=\tilde{V}_1[0] \tag{33}$$

However, when n=1, there is a nonzero contribution from the second term on the RHS of Equation (31) since one term contains $$\frac{\partial}{\partial k}(k) = 1$$

and the remaining factors are non-zero, in general. The second term on the RHS in Equation (32) remains zero since $$\frac{\partial}{\partial k}[k \sin[k(z'' - z')]]_{k=0} = 0 \qquad (34)$$

and we thus conclude that $$V[1] = \tilde{V}[1] \qquad (35)$$

Thus, the approximation to the interaction produced by the Volterra formalism yields correct values for V[0] and V[1] while the Fredholm-based Born series yields the correct values only for V[0]. In another portion of this application, we will present a complete inversion scheme based on moment of V using the iterated Volterra-Born series [9A]. We comment that the first order Volterra approximation, $\tilde{V}_1$ is not as sensitive to the near-field effects as the first order Fredholm approximation, $V_1$.

We now turn to consider the Volterra-based inversion for interactions that can be expressed as sums of Dirac delta functions.

IV. Volterra-Based Inverse Scattering Treatment for Sums of Dirac Delta Functions Rodberg and Thaler [10] have presented an interesting derivation of Fredholm's method for solving the Lippmann-Schwinger equation that involves writing the interaction as a sum of Dirac delta functions. Essentially they argue that since $$V(z) = \int_{\infty}^{+\infty} dz' \delta(z' - z) V(z') \qquad (36)$$

holds for reasonable interaction functions, one can write V(z) as a limit $$V(z) = \lim_{\Delta_j \to 0} \sum_j \Delta_j \delta(z_j - z) V(z_j) \qquad (37)$$

While care must be exercised with such an argument (as shown in more detail in Appendix B), it suggests that a useful model, especially for a scattering interaction having effective compact support and which is also effectively band-limited (of course, both are not rigorously possible simultaneously), can be taken to be $$V(z) = \sum_{j=1}^{J} \Delta_j \delta(z_j - z) V(z_j) \qquad (38)$$

where J is the finite number of delta functions needed to represent the inter-action adequately. (By using Hermnite distributed approximating functionals (HDAFs), $\delta_M(z-z_j|\sigma)$) to replace the delta functions, we can obtain the smooth, well-behaved interaction form $$V(z) = \sum_j \delta_M(z - z_j|\sigma) V(z_j) \qquad (39)$$

about which we later make some brief comments in Appendix B. In this section of the application, we shall focus primarily on Equation (38).)

We recall that the Volterra-based solution of the 1-D scalar Helmholtz equation is [7]

$$\tilde{\psi}_k(z) = \frac{e^{ika}}{2\pi} + k \int_{-\infty}^{+\infty} dz' \sin[k(z' - z)] H(z' - z) V(z') \tilde{\psi}(z') \qquad (40)$$

For the interaction Equation (38), this is seen to give $$\tilde{\psi}_k(z) = \frac{e^{ika}}{2\pi} + k \sum_{j=1}^{J} \sin[k(z_j - z)] H(z_j - z) \Delta_j V(z_j) \tilde{\psi}(z_j) \qquad (41)$$

We assume, without loss of generality, that $$z_j > z_{j-1} \qquad (42)$$

In terms of the full Green's operator, we have that $$\tilde{\psi}_k(z) = \langle z|k \rangle + \langle z|\tilde{G}V|k \rangle \qquad (43)$$

which, making use of the well known expansion $$G = \sum_{j=0}^{\infty} (\tilde{G}_0 V)^j \tilde{G}_0 \qquad (44)$$

give rise to $$\tilde{\psi}_k(z) = \qquad (45)$$

$$\langle z|k \rangle + \sum_{n=1}^{\infty} \langle z|(\tilde{G}_0 V)^n |k \rangle = \langle z|k \rangle + \sum_{n=1}^{\infty} \int_{z<\varsigma_1}^{\infty} d\varsigma_1 \int_{\varsigma_1<\varsigma_2}^{\infty} d\varsigma_2 \ldots$$

$$\int_{\varsigma_{n-1}<\varsigma_n}^{\infty} d\varsigma_n \langle z|\tilde{G}_0 V|\varsigma_1 \rangle \langle \varsigma_1|\tilde{G}_0 V|\varsigma_2 \rangle$$

$$\ldots \langle \varsigma_{n-1}|\tilde{G}_0 V|\varsigma_n \rangle \langle \varsigma_n|k \rangle$$

Here, for clarity we have used $\varsigma$ instead of z as the symbol to represent the ordered coordinate integration variables. This formula is general, but if we now introduce the interaction of Equation (38) the integrals can be evaluated to yield $$\tilde{\psi}_k(z) = \langle z|k\rangle + \sum_{n=1}^{\infty} \sum_{z<\varsigma_1}^{z_J} \sum_{\varsigma_1<\varsigma_2}^{z_J} \ldots \qquad (46)$$

$$\sum_{\varsigma_{n-1}<\varsigma_n}^{z_J} \langle z|\tilde{G}_0 V|\varsigma_1\rangle\langle\varsigma_1|\tilde{G}_0 V|\varsigma_2\rangle \ldots \langle\varsigma_{n-1}|\tilde{G}_0 V|\varsigma_n\rangle\langle\varsigma_n|k\rangle$$

where $\varsigma_1$ through $\varsigma_n$ are now elements of an ordered subset of the z-points where the &functions of the interaction are located. Let $N_z \leq J$ be the number of such points greater than z, then the number of ordered sets of $\varsigma$-points satisfying the limits on the summations is given by the binomial coefficient $N_z!/[n!(N_z-n)!]$. The sum $$\sum_{z<\varsigma_1}^{z_J} \sum_{\varsigma_1<\varsigma_2}^{z_J} \ldots \sum_{\varsigma_{n-1}<\varsigma_n}^{z_J},$$

which for conciseness we write as $\Sigma_{\varsigma_1,\varsigma_2,\ldots,\varsigma_n}$ is the sum over all $N_z!/[n!(N_z-n)!]$ sets. Finally, we have that $$\tilde{\psi}_k(z) = \qquad (47a)$$

$$\langle z|k\rangle + \sum_{n=1}^{N_z} \sum_{\varsigma_1,\varsigma_2,\ldots\varsigma_n} \langle z|\tilde{G}_0 V|\varsigma_1\rangle\langle\varsigma_1|\tilde{G}_0 V|\varsigma_2\rangle \ldots \langle\varsigma_{n-1}|\tilde{G}_0 V|\varsigma_n\rangle\langle\varsigma_n|k\rangle$$

$$\tilde{\psi}_k(z) = \qquad (47b)$$

$$\langle z|k\rangle + \sum_{n=1}^{N_z} (k\Delta)^n \sum_{\varsigma_1,\varsigma_2,\ldots\varsigma_n} \sin(k[\varsigma_1 - z])V(\varsigma_1)\sin(k[\varsigma_2 - \varsigma_1])V(\varsigma_2)$$

$$\ldots \sin(k[\varsigma_n - \varsigma_{n-1}])V(\varsigma_n)\langle\varsigma_n|k\rangle$$

It is clear that the number of terms contributing to $\tilde{\psi}_k(z)$, for any value of z, is $$1 + \sum_{n=1}^{N_z} \frac{N_z!}{n!(N_z-n)!} = 2^{N_z},$$

which is finite (again assuming the number of delta functions in the interaction to be finite). Thus, for $z \geq z_J$, $N_z = 0$ and only one term contributes to $\tilde{\psi}_k(z)$. That is $$\tilde{\psi}_k(z) = \langle z|k\rangle \qquad (48)$$

Similarly, for $z_J > z \geq z_{J-1}$, $N_z = 1$ and we have $$\tilde{\psi}_k(z) = \langle z|k\rangle + k\Delta_J \sin(k[z_J-z])V(z_J) \langle z_J|k\rangle \qquad (49)$$

and for $z_{J-1} > z \geq z_{J-2}$, $N_z = 2$ and $$\tilde{\psi}_k(z) = \langle z|k\rangle + \qquad (50)$$

$$k\Delta_J \sin(k[z_J - z])V(z_J)\langle z_J|k\rangle +$$

$$k\Delta_{J-1} \sin(k[z_{J-1} - z])V(z_{J-1})\langle z_{J-1}|k\rangle +$$

$$k^2\Delta_{J-1}\Delta_J \sin(k[z_{J-1} - z])V(z_{J-1})\sin(k[z_J - z])V(z_J)\langle z_J|k\rangle$$

etc. As one progresses in this manner from the transmission to the reflection region, the number of terms proliferate, but they are individually quite simple. Finally, in the reflection region the number of terms in the wave function is two raised to the number of scattering points in the interaction. Obviously, if we had such a progression of $\tilde{\psi}_k$ values it would be trivial to solve for the various $V(z_j)$ values sequentially starting from the transmission end.

It is instructive to express this result using an $N_z+1$ dimensional vector representation where one component stands for the point z and the other $N_z$ components represent the delta function points in the interaction on the transmission side of z. To this end we introduce a set of $N_z+1$ orthogonal unit vectors $|0\rangle$, $|1\rangle$, $|2\rangle$ ... $|N_z\rangle$, where $|0\rangle$ is the unit vector associated with z. Here we use Dirac notation with $|j\rangle$ representing the $j^{th}$ unit vector in this finite dimensional space. Then we have that $\{s|t\} = \delta_{s,t}$ and the identity matrix in this space is given by $$1 = \sum_{s=0}^{N_z} |s\rangle\langle s| \qquad (51)$$

We next define the matrix Y by $$\{j|Y|l\} = \sin(k[z_l-z_j])V(z_l)\Delta_l \qquad (52)$$

Then $$\tilde{\psi}_k(z) = \qquad (53)$$

$$\{0|[1+kY|1\rangle\{1|][1+kY|2\rangle\{2|] \ldots [1+kY|N_z\rangle\{N_z|]\sum_{l=0}^{N_z} |l\rangle\langle z_l|k\rangle$$

which provides an explicit summation of the Volterra-Born series for this interaction. Physically, we see that each scattering center (i.e., delta function) in the interaction either produces a reflection or it has no effect. Hence the wavefunction at any point is only aware of the scattering centers that lie to the transmission side. The Volterra-Born series at a point z is simply a finite sum of the $2^N$= possibilities. Finally, if we knew $\tilde{\psi}_k(z)$ in the reflection region at as many values of k as there are scattering points in the interaction we could in principle solve the resulting (highly non-linear) equations for the $V(z_j)$. We stress that such a procedure corresponds to using far-field measurements to determine near-field quantities exactly (essentially, one is obtaining the $\tilde{\psi}_k(z_j)$).

One could, of course, follow exactly the same procedure in the Fredholm case starting with $$\tilde{\psi}_k^+(z) = \langle z|k\rangle + \langle z|G^+V|k\rangle \qquad (54)$$

However, in this case there is no Heaviside-function in the coordinate representation of the Green's operator and consequently the counterpart to Equation (46) does not have an ordered sum. The result is that the sum of terms contributing to $$\psi_k^+(z)$$

for any value of z is infinite. This simple interaction illustrates the comparative convergence properties of the Fredholm-Born and Volterra-Born series.

We next note that the $\tilde{T}$-matrix element $$\langle -k|\tilde{T}_k|k\rangle = \langle -k|V|\tilde{\psi}_k\rangle = \sum_{j=1}^{J} e^{ikz_j} V(z_j)\Delta_j \tilde{\psi}_z(z_j) \quad (55)$$

From Equation (22), we have that $$V_1(z) = \int_{-\infty}^{-\infty} dk e^{-2ikz} \sum_{j=1}^{J} e^{ikz_j} V(z_j)\Delta_j \tilde{\psi}_z(z_j) \quad (56)$$

and thus, from Equation (50), we see that the general form of $\tilde{\psi}_k(z_j)$ is $$\tilde{\psi}_k(z_j) = \langle z_j|k\rangle + R(k) \quad (57)$$

where the various terms in R(k) have two kinds of k dependence. First, each is proportional to a linear or higher power of k and, second, each contains phase factor exponentials (resulting from decomposition of the sine functions). Hence, the k-integral of each term can be evaluated explicitly. The integral of the $(z_j|k)$ terms simply reproduce the original interaction (corresponding to the first order Born approximation), and, since $$k^l e^{-2ikz} = \left(\frac{i}{2}\right)^l \frac{\partial^l}{\partial z^l} e^{-2ikz} \quad (58)$$

the terms arising from R(k) contain first or higher derivatives (with respect to z) of delta functions.

For example, the special case of J=3 is $$V_1(z) = \sum_{j=1}^{3} \Delta_j V(z_j)\delta(z-z_j) +$$

$$\frac{1}{4}\sum_{j=1}^{2}\sum_{j'>j} \Delta_j \Delta_{j'} V(z_j)V(z_{j'})[\delta'(z_{j'}-z)-\delta'(z_j-z)] +$$

$$\frac{\Delta_1\Delta_2\Delta_3}{16}[\delta''(z_3-z)-\delta''(z_2-z)+\delta''(z_1-z)-\delta''(z_1+z_3-z_2-z)] \quad (59)$$

If there are more sampling points in the interaction, the structure remains analogous but there occur higher order derivatives of the Dirac delta functions. Finally, we note that formally (and exactly)

$$\int_{z_j-\Delta_j/2}^{z_j+\Delta_j/2} dz \delta^p(z-z_j) = 0, \; p \geq 1 \quad (60)$$

It follows that averaging $V_1$ in the neighborhood of a sampling point averages all of the higher terms (i.e., the near-field or half-off-shell effects) to zero and we find that $$\int_{z_j-\Delta_j/2}^{z_j+\Delta_j/2} dz V_1(z) = \Delta_j V(z_j) \quad (61)$$

Once the $V(z_j)$ are known, one knows the interaction.

Of course, such averaging is a formal exercise for an interaction that is a sum of delta functions since both V(z) and $V_1(z)$ are not true functions. They only have meaning in terms of delta sequences. However, the operational procedure can be applied to real data to construct an HDAF-approximation where the HDAF is interpreted as a member of a delta sequence. Thus, the suggested procedure would be to take the on-shell (far-field) amplitudes $\langle -k|\tilde{T}_k|k\rangle$ and evaluate $\tilde{V}_1(z)$ by Equation (22). Then one would use some averaging procedure such as that indicated in Equation (61) to obtain approximate expressions for the $\Delta_j V(z_j)$ on a sufficiently dense set of points to construct an acceptable approximation to the true interaction using Equation (39). In the process of this averaging, one is taking account of the effects of near-field terms in the Volterra integral equation.

V. Implementation of the Volterra-Based Inversion

As is evident from Equation (61), if we have the modified reflection coefficient $\langle -k|\tilde{T}_k|k\rangle$, we can evaluate the $V(z_j)$ parameters approximately by a suitable averaging procedure. However, experiments are generally carried out under conditions that do not make direct measurement of $\langle -k|\tilde{T}_k|k\rangle$ possible. But, as shown previously, this quantity is calculated from the physical reflection $\langle -k|T|k\rangle$ and transmission $\langle k|T|k\rangle$ amplitudes [7]. Thus to apply Equations (55), (56) and (61) immediately requires an additional measurement compared to a Fredholm-based inversion. This is the price one pays to obtain the simplified Volterra expressions. It is significant, nevertheless, that even if one cannot measure the transmission $\langle k|T|k\rangle$, the Volterra-based inversion can still be carried out, albeit with substantially greater required effort. This greater effort is the price one must pay to take account of the near-field effects in a direct fashion.

To see how this can be done, we consider the Lippmann-Schwinger equation $$\psi_k^+(z) = e^{ikz} - \frac{ik}{2}\int_{-\infty}^{+\infty} dz' e^{ik|z-z'|} V(z')\psi_k^+(z') \quad (62)$$

For the interaction form of Eq.(38), this yields $$\psi_k^+(z) = e^{ikz} - \frac{ik\Delta}{2}\sum_j e^{ik|z-z_j|} V(z_j)\psi_k^+(z_j) \quad (63)$$

We find the transmission coefficient $$t_k = 1 - \frac{ik}{2}\int_{-\infty}^{+\infty} dz e^{ikz} V(z)\psi_k^+(z) \quad (64)$$

$$= 1 - \frac{ik\Delta}{2}\sum_j e^{-ikz_j} V(z_j)\psi_k^+(z_j)$$

The reflection coefficient similarly is $$r_k = -\frac{ik\Delta}{2}\sum_j e^{-ikz_j} V(z_j)\psi_k^+(z_j) \tag{65}$$

The Volterra normalization is such that $\tilde{t}_k = 1$. To achieve this we note that $$t_k \tilde{\psi}_k(z) = \psi_k^+(z) \tag{66}$$

Then by Equation (64), $$t_k = \frac{1}{1 + \frac{ik\Delta}{2}\sum_j e^{-ikz_j} V(z_j)\tilde{\psi}_k(z_j)} \tag{67}$$

and $$\frac{r_k}{t_k} = \tilde{r}_k \tag{68}$$

Thus, $$r_k \left[1 + \frac{ik\Delta}{2}\sum_j e^{-ikz_j} V(z_j)\tilde{\psi}_k(z_j)\right] = \tilde{r}_k \tag{69}$$

and $$\tilde{V}_1(z) = \int_{-\infty}^{+\infty} d(2k)\frac{2i}{k}\tilde{r}_k e^{-2ikz} \tag{70}$$

yielding $$\tilde{V}_1(z) = \int_{-\infty}^{+\infty} d(2k)e^{-2ikz}\frac{2i}{k}r_k\left[1 + \frac{ik\Delta}{2}\sum_j e^{-ikz_j} V(z_j)\tilde{\psi}_k(z)\right] \tag{71}$$

To use this expression, we substitute for $\tilde{\psi}_k(z\ r)$ using Equation (53), and carry out the averages in Equation (61) to generate a system of nonlinear algebraic equations for the $\tilde{\phi}_k(z_j)$ parameters. The only experimental data then needed are the $r_k$.

VI. Conclusion

In this portion of the application, we have considered the problem of taking account of half-on-shell matrix elements of either $T_k$ or $\tilde{T}_k$. We considered the moments of the interaction expressed in terms of $T_k$ and $\tilde{T}_k$ and proved that $\tilde{V}_1[n]$, n=0, 1 is exact, while only $V_1[0]$ is exact. This suggests that an inversion based on the Volterra scheme is preferred, due to the different manner in which the half-off-shell effects enter. This is further supported by the superior convergence properties of the Volterra-based inverse scattering series. We illustrated these convergence properties using a simple model interaction that is expressed as a sum of Dirac delta functions. It was shown that a formal local average of $\tilde{V}_1$ in the neighborhood of a delta function sampling point yields exactly the desired sampling value, $\Delta_j V(z_j)$. This is, of course, not exactly true for a real interaction. However, as argued by Rodberg and Thaler [10A], using a sufficiently dense sampling, combined with an HDAF replacement of the Dirac delta functions, will yield a reasonable approximation [11A]. It has the advantage that the averaging process is, in essence, taking account of the half-off-shell contributions since it averages them exactly to zero for any interaction constructed as a sum of Dirac delta functions. This delta function approach, strictly speaking, depends on taking a specific form for the interaction, but its application can be very general when the interact parameters are determined as discussed.

Appendix A

The Modification of $$G_{0k}^+$$

by the Factor of $k^2$

Recall that the acoustic and electromagnetic wave scattering (in 1–D) is of the form $k^2 V$. The Lippmann-Schwinger equation is $$|\psi_k^+\rangle = |k\rangle + G_{0k}^+(k^2 V)|\psi_k^+\rangle \tag{72}$$

The transition operator is then defined as $$T_k|k\rangle = V|\psi_k^+\rangle = (V + VG_{0k}^+ k^2 T_k)|k\rangle \tag{73}$$

It is then convenient to absorb the $k^2$-factor into the Green's s function as is done in Equation (2). This $k^2$-factor has a consequence of making a Born-expansion solution for $T_k$ a low-k approximation [6]. This is in sharp contrast to quantum scattering for which it is well known that the Born series always converges for sufficiently large k [8A, 12A]. In the Volterra case, this $k^2$-factor cannot prevent convergence no matter how large k is.

Appendix B

Representation of V(z) using Dirac Delta Functions

In a series of studies [11A] it has been shown that a well behaved function can be represented to controllable accuracy by an HDAF approximation. From this point of view, the model interaction form $$V(z) = \sum_j \delta_M(z - z_j|\sigma)V(z_j) \tag{74}$$

(see Equation (35)), with a suitable choice of the imbedded parameters $V(z_j)$, can be made to approximate any realistic interaction closely. (Of course, a limitless number of delta-function approximations could be utilized, but as we later discuss there are advantages to the HDAF approximation.) If V is effectively compact (and band-limited) then only a finite number of $V(z_j)$ parameters are needed. The Born expansion of the wavefunction is given by $$\psi_k(z) = \langle z|k\rangle + \sum_{n=1}^{\infty} \langle z|(G_0 V)^n|k\rangle \tag{75}$$

where $\psi_k(z)$ and $G_0$ can represent either $\psi_k^+(z)$ and $G_0^+$ or $\tilde{\psi}_k(z)$ and $\tilde{G}_0$. Since V is a local operator $$\langle z|(G_0V)^n|k\rangle = \int_{-\infty}^{+\infty} dz'' \langle z|G_0|z''\rangle V(z'')\langle z''|(G_0V)^{n-1}|k\rangle \quad (76)$$

and hence for this model interaction we have $$\langle z|(G_0V)^n|k\rangle = \qquad (77)$$
$$\sum_j \left\{ \int_{-\infty}^{+\infty} dz'' \langle z|G_0|z''\rangle \delta_M(z''-z_j|\sigma)\langle z''|(G_0V)^{n-1}|k\rangle \right\} V(z_j)$$

Now $\delta_M(z''-z_j|\sigma)$, as a member of a delta sequence, is highly localized around $z_j$. In fact, the degree of localization can be controlled by our choice of the width parameter, $\sigma$. The flexibility of the interaction form, $V(z)$, of Equation (74) to represent any realistic interaction depends on its being "well-tempered," as has been discussed elsewhere [11]. This essentially requires that as $\sigma y$ is decreased the number of $z_j$-points must be increased. By suitably localizing $\delta_M(z''-z_j|\sigma)$ relative to how the rapidly the rest of the integrand varies, we can write $$\int_{-\infty}^{+\infty} dz'' \langle z|G_0|z''\rangle \delta_M(z''-z_j|\sigma)\langle z''|(G_0V)^{n-1}|k\rangle \cong \qquad (78)$$
$$\int_{-\infty}^{+\infty} dz'' \langle z|G_0|z_j\rangle \delta_M(z''-z_j|\sigma)\langle z_j|(G_0V)^{n-1}|k\rangle$$

to arbitrary accuracy while still keeping the number of $z_j$-points in Equation (77) finite. Since $$\int_{-\infty}^{+\infty} dz'' \delta_M(z''-z_j|\sigma) = 1 \qquad (79)$$

we then have that $$\langle z|(G_0V)^n|k\rangle = \sum_j \{\langle z|G_0|z_j\rangle\langle z_j|(G_0V)^{n-1}|k\rangle\} V(z_j) \qquad (80)$$

This is clearly tantamount to making a delta function approximation for $V(z)$. Repeating this process for $\langle z_j|(G_0V)^{n-1}|k\rangle$ etc., we can ultimately reduce the Born expansion of the wavefunction to a form equivalent to that obtained starting with a interaction that is a sum of delta-functions. In this sense the delta-function interaction is quite general, but its application (i.e., in the context of the above discussion, fixing u and the number of sample points) sensitively depends on the particular problem. From the basic theory of Fourier transforms, we know that the variation of the integrand in Equation (78) is controlled by its band-width in Fourier transform space, and, in turn, the band-width controls the width of the spacing between $z_j$-points through the Nyquist relationship. Clearly one wants the band width to be as small as can be reasonably chosen in order to make the sample point spacing as large possible.

At the same time the above discussion, also makes clear that one also wants to minimize the spread of the delta-function approximation about the point $z_j$ in Equation (78). The problem of simultaneously minimizing the band-width and the spread of the delta-function approximation in z-space is addressed through the choice of the delta-function approximation of the form used in Equation (74). It has been shown elsewhere that, in the sense of the Heisenberg Uncertainty Principle, the HDAF approximation (i.e., $\delta_M(z-z_j|\sigma)$) is the best one can do [13A].

The above discussion examines the conditions under which a interaction that is a sum of delta-functions can adequately represent the true interaction. However, it does not justify the procedure of Equation (61) per se since this averaging procedure, which is strictly correct for a delta-function interaction, depends explicitly on the fact that the delta function interaction is not well tempered. Precisely how this procedure should be implemented/modified for a realistic interaction is a subject for further research.

REFERENCES

[1A] T. S. Ho and H. Rabitz, J. Chem. Phys. 90, 5614 (1988) and ibid. 91, 7590 (1989); J. M. Geremia and H. Rabitz, Phys. Rev. A, 64, 022710-1-13 (2001); H. Rabitz, Theor. Chem. Accnts. 109 64 (2003).
[2A] R. Jost and W. Kohn, Phys. Rev. 87, 977 (1952).
[3A] H. E. Moses, Phys. Rev. 102. 559 (1956).
[4A] M. Razavy, J. Acoust. Soc. Am. 58, 956 (1975).
[5A] R. T. Prosser, J. Math. Phys. 10, 1819 (1969), ibid.17, 1775 (1976) and ibid. 21, 2648 (1980).
[6A] A. B. Weglein, F. A. Gasparotto, P. M. Carvalho and R. H. Stolt, Geophys. 62, 1975 (1997).
[7A] D. J. Kouri, and A. Vijay, Phys. Rev. E 67, 046614-1-12 (2003); D. J. Kouri, A. Vijay and D. K. Homan, J. Phys. Chem. A107, 7230 (2003).
[8A] R. G. Newton, *Scattering Theory of Waves and Particles* (Springer-Verlag, New York, 1982).
[9A] D. K. Homan and D. J. Kouri to be published.
[10A] L. S. Rodberg and R. M. Thaler, *The Quantum Theory of Scattering* (Academic Press, New York, 1967) pp. 149–153.
[11A] D. K. Homan and D. J. Kouri in Proc. 3rd Int. Conf. on Math. and Num. Aspects of Wave Propagation. (SIAM, Philadelphia, 1995) pp. 56–83: see also C. Chandler and A. Gibson, J. Approx. Theory 100. 233 (1999).
[12A] M. L. Goldberger amd K. M. Watson, *Collsion Theory*.(Wiley New York, 1964).
[13A] D. K. Homan and D. J. Kouri, Phys. Rev. Lett. 85, 5263 (2000); Phys. Rev. A65, 052106–1 (2002); D. J. Kouri, M. Papadakis, I Kakadiaris and D. K. Homan, J. Phys. Chem. A107, 7318 (2003).

Inverse Scattering Theory: Renormalization of the Lippmann-Schwinger Equation for Quantum Elastic Scattering with Spherical Symmetry VII. Introduction There have been several general approaches to the inverse scattering problem in quantum mechanics. The earlier of those was pioneered by Jost and Kohn[1B] and Moses[2B] and it is based on the Born-Neumann perturbation expansion of the Lippmann-Schwinger integral equation describing quantum scattering. Additional work on the approach includes that of Razavey[3B], Prosser[4B], and most importantly, in the context of the seismic inverse problem, by Weglein and co-workers [5B]. The key mathematical issue in the approach concerns the convergence of the resulting inverse scattering series, and this can be deferred, at least for some aspects of the problem, by considering certain subseries[5B].

The other general approach has been that pursued e.g., by Marchenko[6B] and R. G. Newton[7B]. In these approaches, alternative integral equations (of the Volterra-type) are derived leading to extremely robust behavior under iteration, i.e., absolute convergence independent of interaction strength. So far as we can tell, the principle difficulty associated with these approaches is in the nature of the input data required for their implementation. Indeed, it is true in general for quantum scattering that experiment does not readily provide the quantities that are directly involved in the inversion formulae[7B]. This is in part a consequence of the fact that in quantum mechanics, probabilities rather than amplitudes are observed, thereby leading to ambiguities in phases. The present application is not primarily directed at dealing with this issue, although our results are interesting from this aspect. We shall assume that either measurements of angular distributions are available experimentally since these do provide the sort of phase information that one desires, or that one has access to integral cross sections for a range of collision energies.

The approach which we shall pursue has its origin in the first class of methods [1B–5B]. These methods are most simply formulated in terms of the solution, by iteration, of the Lippmann-Schwinger equation for the transition amplitude. Thus, for structureless particle scattering, in 3-D, one has $$T = V + VG_0^+ T \quad (81)$$

where $$G_0^+ = \frac{1}{E - T - i\varepsilon} \quad (82)$$

$$H = T + V \quad (83)$$

denotes the non-interacting Greens function and the Hamiltonian, H, is the sum of T, the kinetic energy, and V, the interaction responsible for the scattering. We view Equation (81) now as an integral equation for V (rather than for T):

$$V = T - VG_0^+ T \quad (84)$$

Then a power series solution for V in terms of T has the form $$V = T - TG_0^+ T + TG_0^+ TG_0^+ T - \ldots = \sum_j^\infty V_j \quad (85)$$

Such an expression is problematic since it requires knowledge of the off-shell T-matrix elements (which are generally not available since they are equivalent to near-field measurements of the wavefunction). However, for the case of a local potential, we must interpret Equation (85) as a sum of local, effective interactions which (provided the series converges) add up to the true, local interaction. Thus, consider the first order term:

$$V_1 = T \quad (86)$$

an arbitrary off-shell matrix element of this then is of the form $$\langle \vec{k}' | V_1 | \vec{k} \rangle = \langle \vec{k}' | T | \vec{k} \rangle \quad (87)$$

$$= \frac{1}{(2\pi)^3} \int d\vec{r} e^{-i\vec{k}' \cdot \vec{r}} V_1(\vec{r}) e^{-i\vec{k} \cdot \vec{r}} \quad (88)$$

$$= \tilde{V}_1(\vec{k} - \vec{k}') \quad (89)$$

Thus, due to the local character assumed for V (and therefore also for $V_j$, j=1, 2, ... ), we can obtain all needed T-matrix elements for Equation (85) once $V_1(\vec{r})$ is determined [1B–5B]. This results from the inverse Fourier transform of Equation (89), where in particular, we consider backward scattered amplitudes[7B]. Then $\vec{k}' = -\vec{k}$ and $$\tilde{V}_1(2\vec{k}) = \langle -\vec{k} | T | \vec{k} \rangle \quad (90)$$

$$V_1(\vec{r}) = 2 \int d\vec{k} e^{-2\vec{k} \cdot \vec{r}} \tilde{V}_1(2\vec{k}) \quad (91)$$

Notice that all of the matrix elements of T can be gotten from the $\tilde{V}_1(2\vec{k})$, simply from the condition $$\langle \vec{k}' | T | \vec{k}'' \rangle = \tilde{V}_1(2\vec{k}) \quad (92)$$

where $$\vec{k} = \frac{1}{2}(k'' - k') \quad (93)$$

Thus, Equation (85) can also be expressed in the form $$V = V_1 - V_1 G_0^+ V_1 + V_1 G_0^+ V_1 G_0^+ V_1 - \ldots \quad (94)$$

This is all well and good except that it can only lead to well-defined results if the perturbation expansion Equation (89) converges. Unfortunately, this is extremely difficult to ascertain in general and it depends on the strength of interaction, V, the existence of bound states in the spectrum of H and the energy of the collision process, etc. [7B]. In general, the expansion does not converge if the interaction is too strong (or if it supports bound states).

The goal of the present application is to provide an alternative inverse scattering series approach which is guaranteed to converge absolutely, independent of the strength of the interaction. The application is organized as follows. In the next section, we derive a renormalized inverse scattering series and discuss its convergence. In section IX, we discuss the information required to apply the new inversion and in section X we illustrate the approach by applying it to a simple model scattering system. In section XI, we discuss our results.

VIII. Renormalization of the Lippmann-Schwinger Equation

We begin by remembering that Equations (81)–(94) also apply in an appropriately modified form if one considers the various partial wave components. For simplicity, we shall restrict ourselves to spherically symmetric interactions in this application, but the method is general [8B]. The radial Lippmann-Schwinger equation is well known to be [9B]

$$\psi_{lk}^+(r) = j_l(kr) - \frac{2mk}{\hbar} \int_0^\infty dr' r'^2 h_l^+(kr_>) j_l(kr_<) V(r') \psi_{lk}^+(r') \quad (95)$$
$$= j_l(kr) + \int_0^\infty dr' r'^2 G_{l0k}^+(r, r') V(r') \psi_{lk}^+(r')$$

where $r_>(r_\leq)$ is the usual greater (lesser) of the pair (r,r'), $j_l$ is the $l^{th}$ regular spherical Bessel function, $$h_l^+$$

is the $l^{th}$ spherical Hankel function with outgoing wave condition, $$\psi_{lk}^+$$

is the $l^{th}$ partial wave component of the scattering boundary condition solution to the Schrodinger equation, and $$G_{l0k}^+$$

is defined by the second equality in Equation (95). Specifically, $$\psi_{\vec{k}}^+(\vec{r}) = e^{i\vec{k}\cdot\vec{r}} - \frac{1}{4\pi} \int d\vec{r}' \frac{e^{i\vec{k}|\vec{r}-\vec{r}'|}}{|\vec{r}-\vec{r}'|} V(\vec{r}') \psi_{\vec{k}}^+(\vec{r}') \quad (96)$$

$$e^{i\vec{k}\cdot\vec{r}} = \sum_l \sum_m i^l Y_{lm}(\hat{r}) Y_{lm}^*(\hat{k}) j_l(kr) \quad (97)$$

$$-\frac{1}{4\pi} \frac{e^{ik|\vec{r}-\vec{r}'|}}{|\vec{r}-\vec{r}'|} = -\frac{2mk}{\hbar^2} \sum_l \sum_m Y_l^m(\hat{r}) Y_l^m(\hat{r}')^* h_l(kr_>) j_l(kr_<) \quad (98)$$

$$\psi_{\vec{k}}^+(\vec{r}) = \sum_l \sum_m i^l Y_{lm}(\hat{r}) Y_{lm}^*(\hat{k}) \psi_{lk}^+(r) \quad (99)$$

The asymptotic form of $$\psi_{lk}^+(r)$$

(for any $r > r_{max}$ such that V(r)=0) is $$\psi_{lk}^+(r) \to j_l(kr) + T_l^{(1)} h_l^+(kr) \quad (100)$$

where $$T_l^{(1)} \equiv -\frac{2mk}{\hbar^2} \int_0^\infty dr r^2 j_l(kr) V(r) \psi_{lk}^+(r) \quad (101)$$

With this definition, the (unitary) S-matrix, $S_l$, satisfies $$S_l = 1 + 2i T_l^{(1)} \quad (102)$$

implying that $$T_l^{(1)} = e^{i\eta_l} \sin \eta_l \quad (103)$$

Here $\eta_l$ is the usual phase shift, and $$S_l = e^{i\eta_l} \quad (104)$$

It will also prove necessary to define an additional quantity:

$$T_l^{(2)} \equiv -\frac{2mk}{\hbar^2} \int_0^\infty dr r^2 \eta_l(kr) V(r) \psi_{lk}^+(r) \quad (105)$$

We note that in general, $T_l^{(2)}$ is not a directly measured quantity nor is it immediately obtainable from measured quantities. Finally, the differential scattering amplitude, $f(\theta)$, is $$f(\theta) = \frac{1}{k} \sum_l (2l+1) P_l(\cos\theta) T_l \quad (106)$$

where $\theta$ is the angle between the incident relative momentum vector, $\vec{k}$, and the direction of observation, $\hat{r}$. For mathematical simplicity, we shall also assume that the interaction has "compact support", i.e., it is zero outside the range $r_{max}$:

$$V(r) = 0, \quad r > r_{max} \quad (107)$$

In general, however, our results will hold for interactions that are not too singular at r=0 and that tend to zero faster than 1/r, as r→∞. Following Sams and Kouri[10B] and Kouri and Vijay[11B], we rewrite Equation (95) as $$\psi_{lk}^+(r) = j_l(kr) \left[ 1 - \frac{2mk}{\hbar^2} \int_{-\infty}^{+\infty} dr' r'^2 h_l^+(kr') V(r') \psi_{lk}^+(r') \right] - \frac{2mk}{\hbar^2} \int_0^r dr' r'^2 [n_l(kr) j_l(kr') - j_l(kr) n_l(kr')] V(r') \psi_{lk}^+(r') \quad (108)$$

But $$h_l^+(kr') = \eta_l(kr) + i j_l(kr) \quad (109)$$

so we write Equation (108) as $$\psi_{lk}^+(r) = j_l(kr)[1 + T_l^{(2)} + iT_l^{(1)}] - \qquad (110)$$

$$\frac{2mk}{\hbar^2}\int_0^\infty dr' r'^2 [\eta_l(kr) j_l(kr') - j_l(kr)\eta_l(kr')] V(r')\psi_{lk}^+(r')$$

We recognize that the factor, $[1+T_l^{(2)}+iT_{l(1)}]$, while unknown, is simply a constant normalization, so that $$\psi_{lk}^+(r) = u_{lk}(r)[1 + T_l^{(2)} + iT_l^{(1)}] \qquad (111)$$

where $$u_{lk}(r) = j_l(kr) + \int_0^r dr' r'^2 \tilde{G}_{l0k}(r, r') V(r') u_{kl}(r') \qquad (112)$$

$$\tilde{G}_{l0k}(r, r') = -\frac{2mk}{\hbar^2}[\eta_l(kr) j_l(kr') - j_l(kr)\eta_l(kr')] \qquad (113)$$

Equation (112) for $u_{lk}(r)$ has the tremendous virtue, compared to the Lippmann-Schwinger equation for $$\psi_{lk}^+(r),$$

of being a Volterra integral equation and under iteration it converges absolutely and uniformly for all appropriately measurable interactions. This is because the kernel, $\tilde{G}_{l0k}(r, r')V(r')$, is triangular, implying that the Fredholm determinant is identically one[7B]. Consequently, it has no zeros and the Fredholm solution encounters no singular points. This is the best possible mathematical situation one can ever have!

However, we still must address the problem of how to make use of Equation (111), since $T_l^{(2)}$ is not readily available. Before dealing with this, we note that in analogy with our earlier work on acoustic scattering [11 B], we can introduce a partial wave transition operator, $T_l$:

$$V\psi_{lk}^+ = T_l j_l \qquad (114)$$

$$T_l = V + V G_{l0k}^+ T_l \qquad (115)$$

and the Volterra-based auxiliary operators:

$$\tilde{G}_{l0k} = G_{l0k}^+ + \frac{2mk}{\hbar^2}|j_l\rangle\langle h_l^+| \qquad (116)$$

or in the coordinate representation, $$\tilde{G}_{l0k}(r, r') = G_{l0k}^+(r_<, r_>) + \frac{2mk}{\hbar^2} j_l(kr) h_l^+(kr') \qquad (117)$$

Then we define $\tilde{T}_l$ such that $$V u_{kl} = \tilde{T}_l j_l \qquad (118)$$

$$\tilde{T}_l = V + V\tilde{G}_{l0k}\tilde{T}_l \qquad (119)$$

We see that $$T_l = \tilde{T}_l\left(1 - \frac{2mk}{\hbar^2}|j_l\rangle\langle h_l^+|T_l\right) \qquad (120)$$

$$= \tilde{T}_l\left(1 - \frac{2mk}{\hbar^2}|j_l\rangle\langle \eta_l|T_l - \frac{2mk}{\hbar^2}|j_l\rangle\langle j_l|T_l\right) \qquad (121)$$

It follows that $$T_l^{(1)} = \tilde{T}_l^{(1)}[1 + T_l^{(2)} + iT_l^{(1)}] \qquad (122)$$

$$T_l^{(2)} = \tilde{T}_l^{(2)}[1 + T_l^{(2)} + iT_l^{(1)}]$$

We then see that $$T_l^{(1)} = \frac{\tilde{T}_l^{(1)}}{1 - \tilde{T}_l^{(2)} - i\tilde{T}_l^{(1)}} \qquad (123)$$

This relation enables us to express the perturbation expansion of V in terms of $\tilde{T}_l^{(1)}$ and $\tilde{T}_l^{(2)}$ then ultimately in terms of $\tilde{T}_l^{(1)}$. We stress, however, that from Equation (119), $$V = \tilde{T}_l - V\tilde{G}_{l0k}\tilde{T}_l \qquad (124)$$

$$= \tilde{T}_l - \tilde{T}_l\tilde{G}_{l0k}\tilde{T}_l + \tilde{T}_l\tilde{G}_{l0k}\tilde{T}_l\tilde{G}_{l0k}\tilde{T}_l + \cdots \qquad (125)$$

which expression converges absolutely and uniformly independent of the strength of the interaction. We shall again restrict ourselves to local (and for this application, spherically symmetric) interactions, $V(r)$.

We now consider how to determine the $\tilde{V}_j$, defined by $$V = \sum_{j=1}^\infty V_j \qquad (126)$$

$$\tilde{V}_1 = \tilde{T}_1 \qquad (127)$$

$$\tilde{V}_2 = -\tilde{V}_1 \tilde{G}_{l0k} \tilde{V}_1 \qquad (128)$$

$$\tilde{V}_3 = \tilde{V}_1 \tilde{G}_{l0k} \tilde{V}_1 \tilde{G}_{l0k} \tilde{V}_1 = -\tilde{V}_2 \tilde{G}_{l0k} \tilde{V}_1 \qquad (129)$$

$$\tilde{V}_j = \tilde{V}_{j-1} \tilde{G}_{l0k} \tilde{V}_1 \qquad (130)$$

$$\tilde{V}_{1l}^{(1)} \equiv -\frac{2mk}{\hbar^2} \int_0^\infty dr\, r^2 j_l^2(kr) \tilde{V}_1(r) \quad (131)$$

$$\tilde{V}_{1l}^{(2)} \equiv -\frac{2mk}{\hbar^2} \int_0^\infty dr\, r^2 \eta_l(kr) \tilde{V}_1(r) j_l(kr) \quad (132)$$

We have written the upper limit as $\infty$ rather than $r_{max}$ in anticipation of the fact that, provided $\tilde{V}_1(r)$ tends to zero faster than $1/r^2$, the more general result holds. It is not difficult then to show that $$T_l^{(1)} = \frac{\tilde{V}_{1l}^{(1)}}{1 - \tilde{V}_{1l}^{(2)} - i\tilde{V}_{1l}^{(1)}} \quad (133)$$

$$T_l^{(2)} = \frac{\tilde{V}_{2l}^{(1)}}{1 - \tilde{V}_{1l}^{(2)} - i\tilde{V}_{1l}^{(1)}} \quad (134)$$

These results have some extremely interesting features. First, note that both $\tilde{V}_{1l}^{(1)}$ and $\tilde{V}_{1l}^{(2)}$ are purely real. Consequently, Equation (133) guarantees satisfaction of the optical theorem, since $$\mathrm{Im}\, T_l^{(1)} = |T_l^{(1)}|^2 \quad (135)$$

(This also implies that one cannot eliminate $V_{1l}^{(2)}$ in favor of $V_{1l}^{(1)}$ by using the real and imaginary parts of Equation (133)). Second, Equation (133) is sufficient to enable an inversion, provided that $T_l(1)$ is known. Thus, Equation (133) is viewed as an equation that is satisfied by the first order radial function, $\tilde{V}_1(r)$:

$$T_l^{(1)}(k) = \frac{-\frac{2mk}{\hbar^2}\int_0^\infty dr\, r^2 j_l^2(kr)\tilde{V}_1(r)}{1 + \frac{2mk}{\hbar^2}\int_0^\infty dr\, r^2 \eta_l(kr)\tilde{V}_1(r) j_l(kr) + \frac{2mk}{\hbar^2}\int_0^\infty dr\, r^2 j_l^2(kr)\tilde{V}_1(r)} \quad (136)$$

Now, of course, the inversion is not so simple since one no longer has Cartesian Fourier transforms to invert. One procedure is to express $\tilde{V}_1(r)$ in some basis set (e.g., Bessel functions); an alternative is to use the distributed approximating functionals. In any case, it may be necessary to obtain $\tilde{V}_1(r)$ on a numerical grid. We conclude that the fundamental results are Equations (133)–(134), along with:

$$\tilde{V}_{j+1} = -\tilde{V}_j \tilde{G}_{l0k} \tilde{V}_1, \; j \geq 1 \quad (137)$$

We now turn to discuss the implementation of this approach in terms of measurable quantities.

IX. Experimental Data Requirements for Implementation of the Volterra-Based Inverse Series In quantum mechanical elastic scattering, the optimum measurements are the differential angular distributions, which are determined by $|f(\theta)|^2$. Due to azimuthal symmetry, we, in fact, consider $2\pi|f(\theta)|^2 \sin \theta$:

$$\frac{\partial \sigma(\theta)}{\partial \theta} = \sin\theta \frac{2\pi}{k^2} \left|\sum_l (2l+1) P_l(\cos\theta) T_l^{(1)}\right|^2 \quad (138)$$

Clearly, if sufficient number of scattering angles are measured, one can (in principle) determine the $T_l^{(1)}$. An alternative that avoids having to determine the individual $T_l^{(1)}$ is to use Equation (136) directly, along with an appropriate representation of $\tilde{V}_1(r)$ to derive a system of inhomogeneous (non-linear) algebraic equations which can be solved. For example, if we expand $\tilde{V}_1(r)$ in a basis, $\{\phi_p(r)\}$, $$\tilde{V}_1(r) = \sum_p \tilde{V}_{1p} \phi_p(r) \quad (139)$$

it can then be seen that $$\frac{\partial \sigma(\theta)}{\partial \theta} = \sin\theta \frac{2\pi}{k^2} \left|\frac{\sum_l (2l+1) P_l(\cos\theta) \sum_p \tilde{V}_{1p} J_{lp}}{1 - \sum_{p'} \tilde{V}_{1p'} H_{1p'}}\right|^2 \quad (140)$$

where $$J_{lp} = -\frac{2mk}{\hbar^2} \int_0^\infty dr\, r^2 j_l^2(kr)\phi_p(r) \quad (141)$$

and $$H_{lp} = -\frac{2mk}{\hbar^2} \int_0^\infty dr\, r^2 h_l^+(kr) j_l(kr)\phi_p(r) \quad (142)$$

In general, Equation (140) would be solved by a least square method, using more $\theta$-values than the number of terms in the expansion over p, Equation (139). The redundancy is useful for averaging out noise. Another alternative is to use angular measurements at a small number of $\theta$'s, but for a range of collision energies ($E=\hbar^2 k^2/2m$) to obtain an over-determined set of simultaneous nonlinear algebraic equations to solve.

Another interesting approach can be based on integral cross section measurements. Thus, the integral cross section at energy E is well-known to be $$\sigma(E) = \frac{4\pi}{k^2} \sum_l (2l+1)|T_l|^2 \quad (143)$$

leading to the expression $$\sigma(E) = \frac{4\pi}{k^2} \sum_l (2l+1) \left|\frac{\sum_p \tilde{V}_{1p} J_{lp}}{1 - \sum_{p'} \tilde{V}_{1p'} H_{lp'}}\right|^2 \quad (144)$$

One must evaluate $\sigma(E)$ at enough energies to generate the requisite algebraic equations for the $\tilde{V}_{1p}$. In expression (140) and (144), it is clear that lower energy measurements will be numerically less complicated because the partial wave expansion will converge with fewer angular momentum states. However, we also expect that (at least for potentials with a repulsive core) the short range part of the potential will be less accurate than the longer range, if one uses low energy data.

It is important to note that in the case of the integral cross section approach, one makes no use of phase-dependent effects; indeed, only the $|T_l|^2$ enter the expression. Neither the basis set nor DAF approaches necessarily require knowledge of the phase of the $T_l$, but one speculates that an inversion based on angular measurements will be more robust (in terms of accuracy) than one based on integral cross section measurements. This remains to be tested. If either the integral or differential cross section approach proves to be feasible, this will represent an extremely attractive feature compared to approaches that require determination of the individual partial wave phase-shifts.

Finally, we point out that once $\tilde{V}_l(r)$ is known, all higher order $\tilde{V}_j(r)$ can be computed in the coordinate representation, using Equation (137). We notice that the same radial functions, $\tilde{V}_j(r)$, result no matter which partial wave is considered. This is a consequence of the assumed spherical symmetry of the original potential. This provides an internal consistency condition that must be satisfied.

Of course, the above ideas, while formally correct, still must be tested on actual experimental data. An important issue is that of the effects of noise and inaccuracies in the data. In this regard, DAF-based methods may offer advantages. In a DAF approach, an approximation to the identity, of the form $$\delta_M(r - r' | \sigma) = \sum_{n=0}^{M} \phi_n(0) \phi_n^* \left( \frac{r - r'}{\sigma} \right) \qquad (145)$$

is employed. Generally, it has the properties that $$\lim_{M \to \infty} \delta_M(r - r' | \sigma) = \delta(r - r') \qquad (146)$$

and $$\lim_{\sigma \to 0} \delta_M(r - r' | \sigma) = \delta(r - r') \qquad (147)$$

here $\sigma$ is a length-scale parameter. For finite M or nonzero $\sigma$, $\delta_M(r-r'|\sigma)$ is not a projector onto an orthogonal subspace of Hilbert space (though it is, usually, such a projector onto the Schwartz subspace). The DAF approximation (which can be made arbitrarily accurate) to the potential is then $$\tilde{V}_1(r) = \int_0^\infty dr' r'^2 \, \delta_M(r - r' | \sigma) \tilde{V}_1(r') \qquad (148)$$

$$= \sum_{n=0}^{M} \phi_n(0) \int_0^\infty dr' r'^2 \, \phi_n^* \left( \frac{r - r'}{\sigma} \right) \tilde{V}_1(r') \qquad (149)$$

If we evaluate the integral by quadrature, then $$\tilde{V}_1(r) \equiv \sum_p W_p r_p^2 \delta_M(r - r_p | \sigma) \tilde{V}_{1p} \qquad (150)$$

and the $\tilde{V}_{1p}$ in this approach are seen to be the discrete, point-wise samples of the first order potential. Clearly, one will obtain expressions for $d\sigma/d\theta$ and $\sigma(E)$ that are entirely analogous to those resulting from the basis set expansion approach. Both methods require the solution of nonlinear algebraic equations and the same experimental data is employed.

X. A Simple Example

By far the simplest scattering problem to solve from the point of view of the Lippmann-Schwinger equation is for a local, Dirac delta function potential. In our first study of inverse acoustic scattering, we found that the Volterra-based series converged to the exact result in a single term. A simple 3-D analogue is the spherically symmetric potential $$V(r) = \lambda \delta(r - r_0) \qquad (151)$$

It can then be shown that the exact transition amplitude is $$T_l^{(1)} = \frac{-\frac{2mk}{\hbar^2} \lambda r_0^2 j_l^2(kr_0)}{1 + \frac{2mk}{\hbar^2} \lambda r_0^2 \eta_l(kr_0) j_l(kr_0) + \frac{2mk}{\hbar^2} \lambda r_0^2 j_l^2(kr_0)} \qquad (152)$$

Given such detailed input, we can use Equation (136) directly:

$$\frac{\lambda r_0^2 j_l^2(kr_0)}{1 + \frac{2mk}{\hbar^2} \lambda r_0^2 \eta_l(kr_0) j_l(kr_0) + \frac{2mk}{\hbar^2} \lambda r_0^2 j_l^2(kr_0)} = \qquad (153)$$

$$\frac{\int_0^\infty dr \, r^2 j_l^2(kr) \tilde{V}_1(r)}{1 + \frac{2mk}{\hbar^2} \int_0^\infty dr \, r^2 \eta_l(kr) \tilde{V}_1(r) j_l(kr) + \frac{2mk}{\hbar^2} \int_0^\infty dr \, r^2 j_l^2(kr) \tilde{V}_1(r)}$$

Obviously, the solution is (independent of the partial wave considered)

$$\tilde{V}_1(r) = \lambda \delta(r - r_0) \qquad (154)$$

Next, we must evaluate the higher order terms in the expansion of V(r) in terms of the $\tilde{V}_j(r)$. By Equation (137), $$\tilde{V}_2(r) = -\tilde{V}_1 \tilde{G}_{l0k} \tilde{V}_1 \qquad (155)$$

$$= -\lambda \delta(r - r_0) \int_0^\infty dr' \, \tilde{G}_{l0k}(r, r') \lambda \delta(r' - r_0) \qquad (156)$$

$$= -\lambda \delta(r - r_0) \tilde{G}_{l0k}(r_0, r_0) \qquad (157)$$

Clearly, due to the behavior of $\tilde{G}_{l0k}(r_0, r_0)$, $\tilde{V}_2(r)$ is identically zero, no matter what that value of l. Further, by Equation (137), all higher $\tilde{V}_j$'s are also zero. We conclude that $$V(r) = \sum_j \tilde{V}_j(r) \equiv \lambda\delta(r - r_0) \qquad (158)$$

Thus, the Volterra-based inverse series again converges to the exact result in a single term.

Of course, in general, one does not know the individual $T_j$s. In this model problem, the differential scattering amplitude is $$f(\theta) = -\frac{2mkr_0^2}{\hbar^2} \frac{\sum_l (2l+1)P_l(\cos\theta)j_l^2(kr_0)}{1 + \frac{2mk}{\hbar^2}\lambda r_0^2 h_l^+(kr_0)j_l(kr_0)} \qquad (159)$$

and the cross section is the square of its modulus. The convergence of this partial wave series results from the property of the Bessel functions, $j_l(kr_0)$, that $j_l(kr_0) \to 0$ for $l > kr_0$. Again, one can in principle obtain sufficient equations and obtain the exact result. The basic conclusion is the same, namely that the Volterra inversion converges to the exact result in a single term.

XI. Discussion of Results

In this application we have presented a new approach to the inverse scattering problem in quantum mechanics. Although attention was focused on purely elastic scattering by spherically symmetric potential, the method is quite general. Indeed, it not only can be applied to quantum scattering, but to many other types of processes. Any process that can be described by a Lippmann-Schwinger type, causal (or anticausal) integral equation should be amenable to the approach. The method is based on a renormalization transformation of the Lippmann-Schwinger Fredholm equation to obtain a Volterra integral equation. In quantum scattering, such equations are well known but principally used to analyze the analytic structure of the S-matrix. An exception is the earlier work of Sams and Kouri[10B], who utilized the renormalization point of view to develop a noniterative numerical method for directly solving for the coordinate representation of the T-matrix. The principal benefit of the renormalization to a Volterra equation for inverse scattering is the fact that their noniterative solutions converge absolutely and (under relatively mild conditions) uniformly independent of the strength of the interaction. This feature allows us to utilize the Volterra equations in a manner similar to that pioneered by Jost and Kohn[1B], Moses[2B] and most recently by Weglein[5B], but with the guarantee that the inverse series always converges.

In the case of quantum scattering in 3-D, the results are complicated by the facts that (a) the renormalization factor is no longer a directly measurable quantity as it is for acoustic scattering in 1-D, (b) the different partial waves do not separate in a simple fashion, (c) the equations which one must solve to determine the potential are nonlinear, due to the intrinsic nature of quantum mechanics. However, there are no difficulties in principle with the present method. Furthermore, the present inverse series does not require the determination of phases. It can, at least in principle, be applied either to differential or integral cross section measurements. If it indeed is the case that sufficiently accurate results can be obtained without requiring determination of phase sensitive quantities, this will provide a major advantage over other inversion equations for quantum scattering.

For the case of scattering by a spherically symmetric Dirac delta function potential, the convergence to the exact result is obtained with a single term. By contrast, the Born-Neumann inverse series based on the Lippmann-Schwinger equation yields the result $$\int_0^\infty dr\, r^2 V_1(r) j_l^2(kr) = T_l^{(1)} \qquad (160)$$

for the first order, effective local interaction. It is immediate that any real $V_1$ obtained from the above will introduce unphysical behavior since the left hand side of the equation is real; i.e., Equation (160) manifestly violates the optical theorem for real $V_l(r)$. Comparing this to Equation (132) and using (152) leads to $$-\frac{2mk}{\hbar^2}\int_0^\infty dr\, r^2 V_1(r) j_l^2(kr) = \frac{-\frac{2mk}{\hbar^2}\lambda_0^2 j_l^2(kr_0)}{1 + \frac{2mk}{\hbar^2} r_0^2 \lambda h_l^+(kr_0) j_l(kr_0)} \qquad (161)$$

a solution of this equation is seen to be $$V_1(r) = \frac{\lambda\delta(r - r_0)}{1 + \frac{2mk}{\hbar^2}\lambda r_0^2 h_l^+(kr_0) j_l(kr_0)} \qquad (162)$$

The second order correction is $$V_2(r) = \frac{-\lambda^2 \delta(r - r_0) G_{l0k}^+(r_0, r_0)}{\left[1 + \frac{2mk}{\hbar^2}\lambda r_0^2 h_l^+(kr_0) j_l(kr_0)\right]^2} \qquad (163)$$

$$\neq 0 \qquad (164)$$

Thus, in this case, the first order term of the series does not yield the exact answer in general, and it does not consist of a single nonzero term. In fact, one can then see that one must sum the infinite series analytically in order to obtain the correct result for values of $\lambda$ that are outside the convergence limit of the series. Equation (160) corresponds to the first term in the Taylor expansion of the denominator on the right hand side of Equation (161), which is analogous to the situation we encountered in our previous work on 1D inverse acoustic scattering. Such an expansion converges only for sufficiently small-values (as well as also depending on the value of $r_0$). Of course, it does permit one to sum the infinite series analytically to obtain the result that holds outside the convergence limits of the series itself [11B]. As is also usual for the Born-Neumann expansion in quantum scattering, the approximation does eventually converge for high enough energy, E (large enough k).

We are currently exploring the inversion of quantum 3D elastic scattering by a nonspherical target, as well as various other wave phenomena. Of particular interest are the cases of acoustic and electromagnetic scattering in full 3D. In addition, we shall carry out test calculations to verify that one can use non-phase sensitive, integral cross sections to carry out an inversion. These results will be reported as they are obtained.

REFERENCES

[1B] R. Jost and W. Kohn, Phys. Rev. 87, 977 (1952).
[2B] H. E. Moses, Phys. Rev. 102, 559 (1956).
[3B] M. Razavy, J. Acoust. Soc. Am. 58, 956 (1975).
[4B] R. T. Prosser, J. Math. Phys. 10, 1819 (1969); ibid., 17, 1775 (1976); ibid., 21, 2648 (1980).
[5B] A. B. Weglein, K. H. Matson, D. J. Foster, P. M. Carvalho, D. Corrigan, and S. A. Shaw, Imaging and inversion at depth without a velocity model: theory, concepts and initial evaluation, Soc. Exploration Geophysics 2000, Expanded Abstracts, Calgary, C A; A. B. Weglein and R. H. Stolt, Migration-inversion revisited, in The Leading Edge (1999) 950. See also the subseries approach to removing multiples from seismic data in A. B. Weglein, F. A. Gasparotto, P. M. Carvalho, and R. H. Stolt, Geophysics 62, 1775 (1997).
[6B] marchenko
[7B] R. G. Newton, Scattering Theory of Waves and Particles (Springer-Verlag, New York, (1982).
[8B] D. J. Kouri (To be published).
[9B] radial
[10B] W. N. Sams and D. J. Kouri, J. Chem. Phys. 51, 4809 and 4815 (1969).
[11B] D. J. kouri and Amrendra Vijay, Phys. Rev. E. (in press).

Inverse Scattering Theory: Renormalization of the Lippmann-Schwinger Equation for Acoustic Scattering in One Dimension XII. Introduction The inverse scattering problem has enormous importance both for practical and theoretical applications. The former include hydrocarbon exploration and production, medial imaging of many varieties, nondestructive testing, target identification and location, etc. The latter include relating interactions governing atomic and molecular systems to experimental measurements, determination of the structure of surfaces and condensed matter systems, imaging of nanostructures, etc. In much of the literature, the focus has been on determining the conditions under which the data inversion will yield a unique result and precisely what information is required to make an inversion possible. In terms of algorithms employed for various types of imaging, an important practical tool is the first Born approximation, which assumes that all scattering is direct, involving a single interaction of the probe with the target. Of course, this is known to be incorrect. Indeed, most imaging procedures or algorithms typically make use of some assumed model for the propagation of the probe signal or disturbance in the scattering medium.

Generally, inversion is practical only in their circumstance that there is a sufficiently small difference between the propagation of the probe signal within the target and its "reference propagation" (low contrast between the target and the reference medium). Over the last decade, Weglein and co-workers [1C] have pioneered inverse acoustic scattering methods that do not require an assumed propagation velocity model within the medium. Their approach is based on the early work of Jost and Kohn [2C], Moses [3C] and Razavy [4C] that used the Born-Neumann power series solution of the acoustic Lippmann-Schwinger equation, and a concomitant expansion of the interaction in "orders-of-the-data". Reversion of the Born-Neumann series leads to an order-by-order scheme for evaluating the terms of the series representation of the scattering interaction in terms of the measured data; e.g., only the on-shell reflection amplitude is required to invert for a local interaction. In principle, the method is completely general and requires no prior information about the target or the propagation details of the probe signal within the target.

The only fundamental limitation of the approach appears to be the finite radius of convergence of the Born-Neumann series solution of the acoustic Lippmann-Schwinger equation. This is generally analyzed using the "spectral radius" of the Fredholm kernel of this equation [Morse and Feshbah, [5C]; Newton, [6C]], and in particular by the $L^2$-norm of this kernel. References and very clear discussions of the issues involved in the convergence of the Born-Neumann forward scattering series can be found in [Goldberger and Watson [7C]; Newton [6C]]. Despite this limitation, Weglein and co-workers [1] have made significant progress using this approach by introducing the idea of "subseries" within the Born-Neumann expansion, which are associated with specific inversion tasks. This expresses the inversion series in terms of a set of subtasks which can be carried out separately from one another.

A particularly significant benefit of this approach is the fat that the convergence properties of the subseries studied to date are much more favorable than those of the full Born-Neumann series. Indeed, empirical evidence has been very encouraging regarding the convergence of the inverse series. However, the nature of the kernel of the Lippmann-Schwinger equation, viewed as an equation for the interaction in terms of the T-operator, is such that its maximum eigenvalue always depends on the explicit nature of the on- and off-shell T-matrix and general statements regarding convergence are difficult to obtain [Prosser [8C]].

Another, more robust approach to solving integral equations is that due to Fredholm [9C], which can be viewed as a generalization of the well-known Cramer's method for solving systems of linear simultaneous algebraic equations. Consequently, fundamental to the approach is a continuous generalization of the determinant of coefficients and its minors. Under the circumstances that the integral equation is of the Volterra type, the "Fredholm determinant" can be shown to equal one and the Fredholm solution reduces to a Born-Neumann expansion, all-be-it one that converges absolutely independent of the scattering interaction strength. Consequently, for such Volterra equations, the Born-Neumann expansion possesses the most robust convergence properties for which one can hope.

Some years ago, Sams and Kouri [10C] (for noniterative computations in quantum scattering) and Kouri [11C] (for electromagnetic scattering) showed that one could carry out a renormalization transformation of the Lippmann-Schwinger equation into a Volterra equation form. Although the Volterra equations for quantum scattering were well known [Goldberger and Watson [7C]; Newton [6C]], previous studies had focused almost exclusively on their use for studying the analytic structure of the S-matrix and the scattering state. The work of Kouri and co-workers concentrated on making use of the Volterra form of the scattering equations to create a noniterative computational algorithm. Their approach, however, made essential use of the "triangular" character of the Volterra equation kernel, which in one dimension (1D) is $$K(z, z')=0, z \geq z' \text{ or } K(z, z')=0; z \leq z' \tag{165}$$

combined with a Newton-Cotes quadrature to solve the equations by a noniterative recursion. However, it is also well-known that the property, Equation (165), underlies the extremely robust nature of the convergence of these Volterra equations with respect to an iterative solution [Morse and Feshbah [5C]; Newton [6C]]. Indeed, the Born-Neumann series solution of the Volterra equation converges absolutely, irrespective of the magnitude of the (in general complex) coupling strength of the interaction! Furthermore, the convergence depends on the global behavior of the interaction (essentially whether it is measurable in a particular sense) and not on its smoothness. For 1D interactions having compact support (and for even more general interactions in the case of 3D scattering), the iterative solution of the Volterra equation converges uniformly on any closed domain of definition in the scattering position variable. Again, under certain relatively weak conditions on the interaction, the iterative solution is an entire function of the scattering wave number, k [Newton [6C]].

Thus, the possible benefits of formulating acoustic scattering in terms of Volterra kernels appear substantial. The infinitely large radius of convergence of the Born-Neumann series solution of the Volterra equation is of especial interest from the standpoint of the inverse acoustic scattering approach of Weglein and co-workers [1C]. It seems natural, therefore, to investigate possible benefits of using the renormalization technique as a framework for developing an inverse scattering series. In fact, we shall show that it is possible to establish general, rigorous convergence properties for the inverse acoustic scattering series for the first time, and in the process show that its radius of convergence is also infinite! We shall restrict our discussion here to 1D scattering but our approach is completely general and extends to higher dimensions [12C].

This portion of this application is organized as follows. In Section XIII, we discuss renormalization of the Lippmann-Schwinger equation for acoustic scattering and introduce an auxiliary transition operator, $\tilde{T}$. This is used as the framework to analyze the convergence of the forward scattering Born-Neumann series. The approach is illustrated by applying it to scattering by a Dirac delta function model interaction. In Section XIV, we show the relationship between the interaction as a function of the physical T-operator and as a function of the auxiliary $\tilde{T}$-operator. We next analyze the non-local nature of $\tilde{T}$ in the coordinate representation, and then use the results to establish the convergence properties of the Volterra-based Born-Neumann inverse series for the interaction. We include in this Section an application to the Dirac delta function interaction. Next, in Section XV, the Volterra inverse series is applied to the case of sound scattering by either a square well or barrier. Our conclusions are given in Section XVI.

XIII. Renormalization of the Lippmann-Schwinger Equation

A. Derivation of the Renormalization Transformation and Auxiliary Transition Operator $\tilde{T}$ We assume that the reader is familiar with the acoustic scattering Lippmann-Schwinger equation for the transition operator, T, given by [Razavy [4C]; Goldberger and Watson [5C]; Newton [6C]]

$$T = \gamma V + \gamma V G_{0k}^+ T \qquad (166)$$

where $G_{0k}^+$ is the causal free Green's operator, multiplied by a factor of $k^2$, $$G_{0k}^+ = \frac{k^2}{E - H_0 + i\varepsilon} \qquad (167)$$

$k^2 = E$ (i.e., k is the frequency associated with the incident acoustic wave), $H_0$ governs the "free propagation" of the acoustic wave, and $\Delta V$ is the interaction responsible for the scattering, with $\gamma$ being the coupling parameter characterizing the strength of the interaction. In general, $\gamma$ is complex. The additional factor of $k^2$ results from the fact that in acoustic scattering (as in general for scattering governed by a Helmholtz type wave equation), the interaction responsible for scattering depends on $k^2$. The full acoustic wave propagation (scattering process) is thus governed by the operator H, $$H = H_0 + k^2 \gamma V \qquad (168)$$

The present 1D acoustic scattering problem in the coordinate representation leads to $$T(z, z') = \gamma V(z, z') + \qquad (169)$$
$$\int_{-\infty}^{+\infty} dz'' \gamma V(z, z'') \int_{-\infty}^{+\infty} dz''' G_{0k}^+(z'', z''') T(z''', z')$$

By incorporating this factor of $k^2$ into the Green's function, we are able to treat the remaining portion of the interaction that depends purely on the spatial variation of the scattering interaction. Initially, we restrict ourselves to "local scattering media", so that $V(z, z') = V(z)\delta(z - z')$ and therefore $$T(z, z') = \gamma V(z)\delta(z - z') + \qquad (170)$$
$$\gamma V(z) \int_{-\infty}^{+\infty} dz'' G_{0k}^+(z, z'') T(z'', z')$$

The non-local character of the causal free Green's function, $$G_{0k}^+(z, z''),$$

reflected in its not commuting with $\gamma V$, is responsible for the fact that $T(z, z'')$ is also generally non-local; i.e., it is never diagonal in the coordinate representation (except for a local, Dirac delta function interaction, $V(z, z') = V(z)\delta(z - z') = \lambda \delta(z - z')\delta(z - z_0)$). For 1D causal scattering boundary conditions, $$G_{0k}^+(z, z'')$$

is explicitly $$G_{0k}^+(z, z'') = -\frac{ik}{2} e^{ik|z - z''|} \qquad (171)$$

The general scattering amplitude is determined by the matrix elements of the T-operator, usually computed in the momentum representation, T(k', k''), given by $$T(k', k'') = \langle k'|T|k''\rangle \qquad (172)$$

where in general, k', k'' and the on-energy-shell wave number, $k=\sqrt{E}$ need not be equal to one another. The physical "reflection scattering amplitude", denoted r(k), results when |k'|=|k''|=|k| and k'=−k:

$$r(k) = (-ik\pi)\langle -k|T|k\rangle \qquad (173)$$

In 1D scattering, one can also identify the transmission amplitude, t(k), given by $$t(k) = 1 + (-ik\pi)\langle k|T|k\rangle \qquad (174)$$

In the work of Sams and Kouri [10C], the renormalization transformation to a Volterra equation results from eliminating the |z−z''|-argument in the free Green's function in Equation (170). This is done by dividing the integration over z'' into segments from −∞ to z and from z to ∞:

$$T(z, z') = \gamma V(z)\delta(z - z') - \qquad (175)$$
$$\frac{ik}{2}\gamma V(z)\int_{-\infty}^{z} dz'' e^{ik(z-z'')} T(z'', z') -$$
$$\frac{ik}{2}\gamma V(z)\int_{z}^{+\infty} dz'' e^{-ik(z-z'')} T(z'', z')$$

One then adds and subtracts $$-\frac{ik}{2}\gamma V(z)\int_{z}^{-\infty} dz'' e^{ik(z-z'')} T(z'', z'),$$

and after simple manipulation, one obtains $$T(z, z') = \gamma V(z)\left[\delta(z - z') - \frac{ik}{2}e^{ikz}\int_{-\infty}^{+\infty} dz'' e^{-ikz''} T(z'', z')\right] - \qquad (176)$$
$$\frac{ik}{2}\gamma V(z)\int_{z}^{+\infty} dZ''\left[e^{-ik(z-z'')} - e^{ik(z-z'')}\right] T(z'', z')$$

It can be verified that this is equivalent to writing $$G_{0k}^{+}(z, z'')$$

as $$G_{0k}^{+}(z, z'') = \tilde{G}_{0k}(z, z'') - \frac{ik}{2} e^{ik(z-z'')} \qquad (177)$$

so that $$\tilde{G}_{0k}(z, z'') = -\frac{ik}{2}\left[e^{ik(z''-z)} - e^{-ik(z''-z)}\right] \qquad (178)$$
$$\equiv k\sin[k(z'' - z)], z < z''$$
$$= 0, z \geq z'' \qquad (179)$$

In abstract operator notation, this is $$G_{0k}^{+} = \tilde{G}_{0k} - ik\pi|k\rangle\langle k| \qquad (180)$$

This relation is extremely useful in our subsequent analysis and we shall make much use of it. Notice that the Green's operator $\tilde{G}_{0k}$ differs from the usual causal one, $$G_{0k}^{+},$$

by a solution of the homogeneous equation [Newton, [6C]]:

$$(E - H_0)G_{0k}^{+} = k^2 \qquad (181)$$

$$(E - H_0)\tilde{G}_{0k} = k^2 \qquad (182)$$

$$(E - H_0)\, [-ik\pi|k\rangle\langle k|] = [-ik\pi|k\rangle\langle k|(E - H_0) = 0 \qquad (183)$$

The abstract version of Equation (176) results from substituting Equation (180) into Equation (166):

$$T = \gamma V[1 - ik\pi|k\rangle\langle k|T] + \gamma V\tilde{G}_{0k}T \qquad (184)$$

Next we note that the action of T on the initial state |k⟩ is of the form $$T|k\rangle = \gamma V[1 - ik\pi\langle k|T|k\rangle]|k\rangle + \gamma V\tilde{G}_{0k}T|k\rangle \qquad (185)$$

(unknown) constant, $c_k$, as $$c_k = 1 - ik\pi\langle k|T|k\rangle \equiv \equiv t(k) \qquad (186)$$

we see that $$T|k\rangle = \gamma V c_k|k\rangle + \gamma V\tilde{G}_{0k}T|k\rangle \qquad (187)$$

The relationship between T|k⟩ and the Lippmann-Schwinger pressure state, $$|P_k^{+}\rangle,$$

is $$\sqrt{2\pi}\, T|k\rangle = \gamma V|P_k^{+}\rangle \qquad (188)$$

and thus $$|P_k^+\rangle = \sqrt{2\pi}\, c_k |k\rangle + \tilde{G}_{0k}\gamma V |P_k^+\rangle \qquad (189)$$

Clearly, the factor $C_k$ is simply a normalization constant and one can define an auxiliary pressure state vector $|p_k\rangle$, in relation to $$|P_k^+\rangle,$$

according to $$|P_k^+\rangle = c_k |p_k\rangle \qquad (190)$$

$$|p_k\rangle = \sqrt{2\pi}|k\rangle + \tilde{G}_{0k}\gamma V |p_k\rangle \qquad (191)$$

The coordinate representation, $\langle z|p_k\rangle = p_k(z)$ satisfies $$p_k(z) = e^{ikz} + k \int_z^{+\infty} dz'' \sin[k(z''-z)]\gamma V(z'')p_k(z'') \qquad (192)$$

which is recognized as an inhomogeneous Volterra integral equation of the second kind. We remark here that Volterra equations involving improper limits (i.e., $\pm\infty$) still converge absolutely for $|\gamma|<\infty$, but they must satisfy additional restrictions on the z-dependence of the interaction. This is especially true in order for their iterative solutions to converge uniformly on any closed interval $[z_1, z_2]$. It is sufficient that the interaction $V(z)$ have compact support and $|V(z)|$ be measureable. It remains true even for infinite ranged interactions so long as they decay sufficiently rapidly and are not too singular. This is discussed for similar Volterra equations in [Goldberger and Watson [5C]; Newton [6C]]. Throughout our discussion, we assume that such conditions are met. By Equation (190), Lp*) results from renormalizing $$|P_k^+\rangle$$

according to $$|p_k\rangle = \frac{|P_k^+\rangle}{c_k} \qquad (193)$$

In fact, $c_k$ is essentially the inverse of the Jost function [Newton [6C]]. We remark that the above expression also provides the physial interpretation of the "Volterra pressure wave", $p_k(z)$ [13C]. Clearly, it represents a wave produced by an incident plane wave having an amplitude equal to $1/c_k \equiv 1/t(k)$. This leads to a reeted wave with the amplitude $r(k)|t(k)$ and a transmitted wave with amplitude exatly equal to one. Of course, such an incident wave cannot, in general, be created experimentally since it requires advance knowledge of the effect of the scatterer in the form of $1/t(k)$. However, this does not alter the interpretation of the wave $p_k(Z)$.

Let us now return to Equation (184), and define an auxilliary transition operator, $\tilde{T}$, according to $$T = \tilde{T}[1 - ik\pi|k\rangle\langle k|T] \qquad (194)$$

It can be verified that $$\tilde{T} = \gamma V + \gamma V \tilde{G}_{0k} \tilde{T} \qquad (195)$$

and this is the fundamental equation which will be used to analyze the inverse series for $\gamma V$. (Note that the operator inverse, $[1-ik\pi|k\rangle\langle k|T]^{-1}$, should always exist. This essentially requires that the operator $ik\pi|k\rangle\langle k|T$ not have any eigenvalues equal to $+1$. A worst-case would correspond to the inverse of T being equal to $ik\pi|k\rangle\langle k|$, which cannot occur since T does not commute with $H_0$ while $|k\rangle\langle k|$ does.) It is instructive to evaluate explicitly the normalization constant, $c_k$, in terms of the solution of the Volterra equation. This can be quite done by combining Equations (185), (186) and (194) to write $$T|k\rangle = c_k \tilde{T}|k\rangle \qquad (196)$$

expressed as $$c_k = 1 - ik\pi\langle k|\tilde{T}|k\rangle c_k \qquad (197)$$

so that $$c_k = \frac{1}{1 + ik\pi\langle k|\tilde{T}|k\rangle} \qquad (198)$$

Thus, the renormalized or auxiliary pressure state, $|p_k\rangle$, is given by $$|p_k\rangle = |P_k^+\rangle[1 - ik\pi\langle k|\tilde{T}|k\rangle] \qquad (199)$$

The physical reflection amplitude, $r(k)$, is given by $$r(k) = -ik\pi\langle -k|T|k\rangle = -t(k)ik\pi\langle -k|\tilde{T}|k\rangle \qquad (200)$$

These relations provide us with the necessary tools to express auxilliary amplitudes in terms of the physical amplitudes.

B. Convergence of the Born-Neumann Series for $|p_k\rangle$ and $\tilde{T}$

On one hand, the convergence of the Born-Neumann series for either $$|P_k^+\rangle$$

or T is well-known to depend critically on the size of the coupling constant, $\gamma$(or equivalently, on the size of the "contrast" between the propagation under $H_0$ and that under $H = H_0 + k^2\gamma P$) [Goldberger and Watson [5]; Newton [6]]. On the other hand, it is also well-known that iterative solutions of either Equation (192) or (195) converge absolutely for $|\gamma|\infty$[Newton [6]]. Furthermore, the iteration of Equation (192) converges uniformly on any closed domain of z (for a wide class of interactions). It is useful to stress the origin of this robustness since it turns out to be the basis of the convergence of the Volterra-based inverse series for $\gamma V$. The kernel of Equation (192) can be written (for all z, z″) as $$\gamma K(z, z'') = k\gamma \sin[k(z''-z)]V(z''), \; z < z'' \qquad (201)$$

$$\equiv 0, \; z \geq z'' \qquad (202)$$

According to the discussion in [Newton [6]; see also those in Rodberg and Thaler [14] and Mathews and Walker [15]] one characterizes the convergence in terms of Fredholm's method of solution. This method is the continuum analogue of solving a linear system of algebraic equations, and it expresses the inverse of the integral kernel in terms of the ratio of the first Fredholm minor to the Fredholm determinant, $\Delta$. The determinant $\Delta$ can be expressed as an infinite series of the form (for the acoustic case)

$$\Delta = \sum_{n=0}^{\infty} (\gamma)^n \kappa_n \qquad (203)$$

where $$\kappa_n \equiv T_r(K^n) \qquad (204)$$

It is not difficult to verify that for the Volterra kernel, $K(z, z'')$, above, $$\kappa_n = \delta_{n0} \qquad (205)$$

and consequently, for such kernels, $$\Delta \equiv 1 \qquad (206)$$

regardless of the strength of the scatterer, $\gamma$. Furthermore, by use of Hadamard's theorem [6C, 14C], it then can be proved that the infinite series for the first Fredholm minor converges absolutely and uniformly for $\gamma$ in the entire complex plane (more details are given in the Appendix C). It also has been established [Mathews and Walker [15C]] that when the Fredholm determinant equals one, the Fredholm solution is identical to the Born-Neumann iterative solution of the integral equation. We conclude that iterative solutions of Volterra integral equations possess the most robust convergence possible. While it is true that these convergence properties are independent of the strength of $\gamma$, there are conditions on the analytical structure allowed for the scattering interaction. These have to do with the integrability of any singularities and the behavior at infinity. They are discussed in [Newton [6C]] in some detail. If the interaction has compact support, and is not too singular, then the convergence is of the strongest character (i.e., absolute and uniform, leading to entire functions of wave number k and coupling $\gamma$).

It is therefore clear that the essential property of the Volterra kernel is that it satisfies Equations (201)–(202); as noted in [Newton [6C]], this is the continuous version of the "triangular" property of matries. It is equivalent to the property that the Fredholm determinant of Equation (192) or (195) is identically one. Furthermore, it ensures that the Born-Neumann series for $p_k(Z)$, obtained from Equation (195), is uniformly convergent on any closed domain of z, for a wide class of interactions.

We stress that this is all well-known. We have included it explicitly here because its implications for the inverse scattering series determining $\gamma V$ have never been explicated. In addition, it is perhaps not appreciated that the original Lippmann-Schwinger equation itself can be directly iterated in a fashion that is also everywhere absolutely convergent! Obviously, such an iteration must differ from the straightforward iteration of the Lippmann-Schwinger equation, $$|P_k^+\rangle = \sqrt{2\pi}|k\rangle + G_{0k}^+ \gamma V |P_k^+\rangle,$$

which leads to $$|P_k^+\rangle = \sqrt{2\pi} \sum_{n=0}^{\infty} (G_{0k}^+ \gamma V)^n |k\rangle \qquad (207)$$

the proof of whose convergence depends on the $L^2$-norm of the kernel, $$\|G_{0k}^+ \gamma V\|_2.$$

In fact, wean simply iterate Equation (189) for the Lippmann-Schwinger state $|P_k^+\rangle$:

$$|P_k^+\rangle = \sqrt{2\pi} \sum_{n=0}^{\infty} (\tilde{G}_{0k} \gamma V)^n c_k |k\rangle = \sqrt{2\pi} c_k \sum_{n=0}^{\infty} (\tilde{G}_{0k} \gamma V)^n |k\rangle \qquad (208)$$

We stress that even though $c_k$ is unknown in Equation (208), it is simply a number and can be calculated directly from the known iterate-vectors, $$(G_{0k}^+ \gamma v)^n |k\rangle.$$

Thus, $$c_k = \frac{1}{1 + ik\pi \sum_{n=0}^{\infty} \langle k|\gamma V (\tilde{G}_{0k} \gamma V)^n|k\rangle} = t(k) \qquad (209)$$

This is equivalent to the iterative solution for $|p_k\rangle$ but the point we wish to stress is that the standard, physical Lippmann-Schwinger equation an be iterated in an absolutely convergent fashion, independent of the strength of the interaction. Ofourse, this is simply a reflection of the fact that the Lippmann-Schwinger equation is neither purely a Fredholm or Volterra equation. Therefore, it can manifest the convergence characteristics of either, depending on the manner in which it is written and iterated.

C. Illustrative Example

It is helpful toonsider an example problem in order to appreiate better the vast difference in convergence between the Born-Neumann series based on the Lippmann-Schwinger Fredholm equation and the renormalized Lippmann-Schwinger Volterra equation. A convenient and simple model scattering interaction is the Dirac delta function:

$$\gamma V(z) = \gamma \delta(z - z_0) \qquad (210)$$

The solution to the Lippmann-Schwinger equation is found from noting that $$P_k^+(z) = e^{ikz} - \frac{ik\gamma}{2} e^{ik|z-z_0|} P_k^+(z_0) \tag{211}$$

This implies that $$P_k^+(z_0) = \frac{e^{ikz_0}}{\left(1 + \frac{ik\gamma}{2}\right)} \tag{212}$$

so the exact solution is $$P_k^+(z) = e^{ikz} - \frac{\frac{ik\gamma}{2}}{\left(1 + \frac{ik\gamma}{2}\right)} e^{ikz_0} e^{ik|z-z_0|} \tag{213}$$

The Born-Neumann series solution is given by $$P_k^+(z) = e^{ikz} - \left(\frac{ik\gamma}{2}\right) e^{ikz_0} e^{ik|z-z_0|} \left[1 - \frac{ik\gamma}{2} + \left(\frac{ik\gamma}{2}\right)^2 + \cdots\right] \tag{214}$$

It is clear that the convergence of this series is determined by the requirement $|k\gamma/2|<1$, which is just the condition for the convergence of a power series expansion of $(1+ik\gamma/2)^{-1}$. It is also evident that the Born-Neumann series is convergent only at low energies in this case since $k=\sqrt{E}$, and therefore only for sufficiently low E will the convergence condition be satisfied. This is the opposite of the usual situation that applies to quantum scattering [Goldberger and Watson [5C]]. Of course, in this simple example, one can recognize that the series can be analytically summed to yield the exact result valid at all k and γ. In general, that will not be the case.

We next consider the Born-Neumann series for $p_k(z)$; Equation (192) then becomes $$p_k(z) = e^{ikz} + k \int_z^{+\infty} dz'' \sin[k(z''-z)] \gamma \delta(z''-z_0) e^{ikz''} + \tag{215}$$
$$k^2 \int_z^{+\infty} dz'' \sin[k(z''-z)] \gamma \delta(z''-z_0)$$
$$\int_{z''}^{+\infty} dz''' \sin[k(z'''-z'')] \gamma \delta(z'''-z_0) e^{ikz'''} + \cdots$$

We see that all terms higher than first order in the interaction vanish identically due to the appearance of the factor $\sin[k(z_0-z_0)]$. Thus, for $z \geq z_0$, we obtain exactly $$p_k(z) = e^{ikz} \tag{216}$$

and for $z<z_0$, we obtain exactly $$p_k(z) = e^{ikz} + k\gamma \sin[k(z_0-z)] e^{ikz_0} \tag{217}$$

This does not complete the analysis since we must also evaluate $c_k$ using only information generated by the iterative solution for $p_k(Z)$. This is simple using Equations (196)–(200) and yields $$c_k = \frac{1}{1 + \frac{ik\gamma}{2} \int_{-\infty}^{+\infty} dz e^{-ikz} \delta(z-z_0) p_k(z)} \tag{218}$$

$$= \frac{1}{1 + \frac{ik\gamma}{2} \int_{-\infty}^{+\infty} e^{-ikz_0} p_k(z_0)} \tag{219}$$

But by Equation (216), this gives $$c_k = \frac{1}{1 + \frac{ik\gamma}{2}} \tag{220}$$

Therefore the Born-Neumann series for $$P_k^+(z)$$

based on the renormalized Lippmann-Schwinger equation results in $$P_k^+(z) = \frac{e^{ikz_0}}{\left(1 + \frac{ik\gamma/2}{2}\right)}, z \geq z_0 \tag{221}$$

$$= e^{ikz} - \frac{\frac{ik\gamma}{2}}{\left(1 + \frac{ik\gamma}{2}\right)} e^{2ikz_0} e^{-ikz}, z < z_0 \tag{222}$$

We conclude that the Volterra-based iteration converges to the exact answer with just the first order term, all higher terms being zero. The fundamental difference between the Volterra and Fredholm iterated expressions is that the former does not involve a power series expansion of the normalization factor, $c_k$, whose convergence would have required that $|k\gamma/2|$ be less than one. Instead, $c_k$ has been factored out by renormalizing from $$P_k^+(z)$$

to $p_k(z)$. We emphasize that this renormalization follows for any scattering problem that is expressible in terms of Green's functions $$G_{0k}^{\mp},$$

since it is true in general (for 1D scattering) that $$G_{0k}^{\pm} = \tilde{G}_{0k} \mp ik\pi |k\rangle\langle k| \tag{223}$$

We also note that analogous relationships have been derived for 3D scattering Green's functions. We now turn to consider the inverse scattering series for the interaction, γV.

XIV. The Inverse Scattering Series for γV

A. Fredholm and Volterra Born-Neumann Series for γV

We begin by establishing that distinct Born-Neumann series for γV can be obtained from Equation (166) for T or Equation (195) for T. We solve Equation (166) for γV as $$\gamma V = T(1 + G_{0k}^+ T)^{-1} \tag{224}$$

$$= T(1 + \tilde{G}_{0k} T - ik\pi |k\rangle\langle k|T)^{-1} \tag{225}$$

But Equation (194), this yields $$\gamma V = T([1 - ik\pi|k\rangle\langle k|T] + \tilde{G}_{0k}\tilde{T}[1 - ik\pi|k\rangle\langle k|T])^{-1} \tag{226}$$

$$= T[1 - ik\pi|k\rangle\langle k|T]^{-1}(1 + \tilde{G}_{0k}\tilde{T})^{-1} \tag{227}$$

so that finally, $$\gamma V = \tilde{T}(1 + \tilde{G}_{0k}\tilde{T})^{-1} \tag{228}$$

It follows that, provided they converge, γV can be obtained from either of the following Born-Neumann series expansions:

$$\gamma V = \sum_{n=0}^{\infty} T(G_{0k}^+ T)^n \tag{229}$$

and $$\gamma V = \sum_{n=0}^{\infty} \tilde{T}(-\tilde{G}_{0k}\tilde{T})^n \tag{230}$$

The convergence properties of Equation (229) depend, of course, on the spectral radius of the kernel $$G_{0k}^+ T,$$

which in turn depends crucially on both the on- and off-shell elements of the T-matrix. For this reason, general conclusions regarding the convergence of Equation (229) have been extremely difficult to obtain despite heroic efforts [Prosser [8C]]. We shall see that this is not the case for Equation (230)!

The convergence properties of Equation (230) will be studied using the Fredholm method of solving Equation (228). To do so requires knowledge of the properties of the kernel $\tilde{G}_{0k}\tilde{T}$, which are yet to be established. It is clear, however, that when both expansions converge, they must agree, since convergent power series yield a unique result [Kaplan [16C]]. In order to investigate the convergence of Equation (230), we now consider the non-local character of $\tilde{T}$ in the coordinate representation.

B. Non-local Character of $\tilde{T}$ (z, z')

The aim of this subsection is to establish that $\tilde{T}(z, z') = 0$ when z>z'. It is not difficult to show that Equation (195) has the solution $$\tilde{T} = \gamma V + \gamma V \tilde{G} \gamma V \tag{231}$$

where $$\tilde{G} = \tilde{G}_0 + \tilde{G}_0 \gamma V \tilde{G} \tag{232}$$

(see R. G. Newton, 1982, pp. 343–344; especially Equation 12.42 and the following unnumbered equation). From Equation 12.40a in Newton, we see that $$G^+(k;z,z') = -k\psi^+(k,z_<)f(k,z_>) \tag{233}$$

where $\psi^+$ (k, z) is the regular (physical or causal) scattering solution of the interacting Shrodinger equation and f(k,z) is an irregular solution of the same equation, introduced by Jost [6C]. Then defining an interacting Green's function, $\tilde{G}$(k; z, z'), that vanishes for z≧z', it is easy to see that $$\tilde{G}(k;z,z') = G^+(k;z,z') + k\psi^+(k,z')f(k,z) \tag{234}$$

Obviously, $k\psi^+(k,z')f(k,z)$ satisfies the homogeneous interacting-Green's function Schrodinger equation. Then $$\tilde{G}(z,z') = 0, \; z \geq z' \tag{235}$$

and for local potentials $$\tilde{T}(z, z') = \gamma V(z)\delta(z - z') + \tag{236}$$

$$\gamma^2 \int_{-\infty}^{+\infty} dz'' \int_{-\infty}^{+\infty} dz''' V(z)\delta(z - z'')$$

$$\tilde{G}(z'', z''')V(z''')\delta(z''' - z')$$

or $$\tilde{T}(z,z') = \gamma V(z)\delta(z-z') + \gamma^2 V(z)\tilde{G}(z,z')V(z') \tag{237}$$

It is therefore clear that as a function of either z or z', $\tilde{T}$(z, z') has support determined by V(z) or V(z'). Also, for z>z', the first term on the R.S. of Equation (237) is zero due to the Dirac delta function and the second term is zero due to $\tilde{G}$(z, z'). Therefore, we have proved that $$\tilde{T}(z,z') = 0, \; z > z' \tag{238}$$

Finally, $\tilde{T}$(z, z') has an inerrable singularity at z=z'.

C. Convergence of the Inverse Series for γV

We note next that the kernel of the Volterra-based Born-Neumann series for γV, Equation (238), is given by $$\tilde{K}(z, z') = \langle z|\tilde{G}_{0k}\tilde{T}|z'\rangle \tag{239}$$

It is necessary to compute $\text{Tr}(\tilde{K}^n)$, but it is sufficient to examine $\text{Tr}(\tilde{K}^2)$ to see how the general case behaves:

$$Tr(\tilde{K}^2) = \int_{-\infty}^{+\infty} dz \int_{-\infty}^{+\infty} dz' \tilde{K}(z, z')\tilde{K}(z', z) \tag{240}$$

This can be written as $$Tr(\tilde{K}^2) = \int_{-\infty}^{+\infty} dz_1 \cdots \int_{-\infty}^{+\infty} dz_4 \tilde{G}_{0k}(z_1, z_2)\tilde{T}(z_2, z_3) \tag{241}$$

$$\tilde{G}_{0k}(z_3, z_4)\tilde{T}(z_4, z_1)$$

However, by the Volterra property of $\tilde{G}_{0k}$ and $\tilde{T}$, a nonzero contribution can only occur if $$z_1 > z_4 > z_3 > z_2 > z_1 \quad (242)$$

which clearly is never satisfied. We conclude that the Volterra property is satisfied for the product of two (or more) Volterra kernels and $$Tr(\tilde{K}^2) = Tr(\tilde{K}^n) = 0, \ n \geq 2 \quad (243)$$

It is similarly easy to prove that $Tr(\tilde{K}) = 0$.

We therefore conclude that the Fredholm determinant for Equation (228) equals one. This guarantees that, for a not-too-singular, local interaction having compact support, the Volterra-based inverse scattering series converges absolutely and uniformly independent of the strength of the interaction! This is an amazing result since it ensures that this inverse scattering series always converges for any magnitude (complex) coupling constant.

D. Utilization of the Volterra Inverse Series for $\gamma V$ in Orders of $\tilde{T}$ and the Relation to Data Requirements In order to use the new Volterra inverse series to determine $\gamma V$, the final step is to develop explicit expressions for it in terms of "far-field" measured quantities. The standard Born-Neumann inversion of the Lippmann-Schwinger-based approach, to obtain a local potential, requires knowledge only of the reflection amplitude, r(k), as a function of k. We shall see that additional data are required in order to use the Volterra inverse series. Recall that by Equation (230), $$\gamma V = \sum_{n=0}^{\infty} \tilde{T} - (\tilde{G}_{ok}\tilde{T})^n \quad (244)$$

where $$T = \tilde{T}/[1 - ik\pi|k\rangle\langle k|T] \quad (245)$$

We shall express $\gamma V$ as a power series in orders of $\tilde{T}$:

$$\gamma V = \sum_{n=0}^{\infty} \tilde{\lambda}^j \tilde{V}_j \quad (246)$$

where $$\tilde{V}_j = \tilde{T}(-\tilde{G}_{0k}\tilde{T})^{j-1}, \ j = 1, 2, \quad (247)$$

Next, recall that by Equation (195), $$\tilde{T} = \sum_{n=0}^{\infty} (\gamma V \tilde{G}_{ok})^n \gamma V \quad (248)$$

$$\tilde{\lambda}\tilde{T} = \sum_{n=0}^{\infty} \left( \sum_{j=1}^{\infty} \tilde{\lambda}^j \tilde{V}_j \tilde{G}_{ok} \right)^n \sum_{j'=1}^{\infty} \tilde{\lambda}^{j'} \tilde{V}_{j'} \quad (249)$$

since $\tilde{T}$ is first order in $\tilde{\lambda}$. We then collect coefficients of each power of $\tilde{\lambda}^j$:

$$\tilde{\lambda}^1: \tilde{T} = \tilde{V}_1 \quad (250)$$

$$\tilde{\lambda}^2: 0 = \tilde{V}_2 + \tilde{V}_1 \tilde{G}_{ok} \tilde{V}_1 \quad (251)$$

$$\tilde{\lambda}^3: 0 = \tilde{V}_3 + \tilde{V}_2 \tilde{G}_{ok} \tilde{V}_1 + \tilde{V}_1 \tilde{G}_{ok} \tilde{V}_1 \tilde{G}_{ok} \tilde{V}_1 \quad (252)$$

etc. Matrix elements of these expressions are first evaluated in the k-representation and the results subsequently transformed to the z-representation. This is because the starting expression involves the k-representation matrix elements of $\tilde{T}$. However, using the lower order operators, $\tilde{V}_1$, to express $\tilde{V}_j$ solely in terms of $\tilde{V}_1$ and $\tilde{G}_{0k}$, one can find that, in general, $$\tilde{V}_j = -\tilde{V}_{j-1} \tilde{G}_{ok} \tilde{V}_1 \quad (253)$$

This is the most convenient form with which to evaluate the higher order corrections. The Volterra-based expressions can be compared to the Born-Neumann inverse series based on the usual Lippmann-Schwinger equation [1C–4C]:

$$\gamma V = \sum_{n=0}^{\infty} T(-G_{0k}^+ T)^n = \sum_{j=1}^{\infty} \lambda^j V_j \quad (254)$$

$$T = \sum_{n=0}^{\infty} (\gamma V G_{0k}^+)^n \gamma V \quad (255)$$

and this leads to $$\lambda T = \sum_{n=0}^{\infty} \left( \sum_{j=1}^{\infty} \lambda^j V_j G_{0k}^+ \right)^n \sum_{j'=1}^{\infty} \lambda^{j'} V_{j'} \quad (256)$$

implying then $$\lambda^1: T = V_1 \quad (257)$$

$$\lambda^2: 0 = V_2 + V_1 G_{0k}^+ V_1 \quad (258)$$

$$\lambda^3: 0 = V_3 + V_2 G_{0k}^+ V_1 G_{0k}^+ V_2 + V_1 G_{0k}^+ V_1 G_{0k}^+ V_1 \quad (259)$$

etc. Again, one can show that in general, $$V_j = -V_{j-1} G_{0k}^+ V_1 \quad (260)$$

However, it is crucial to recognize that $$\tilde{V}_j \neq V_j \quad (261)$$

because they correspond to orders of completely different parameters ($\tilde{V}_j$ is jth order in $\tilde{T}$ while $V_j$ is jth order in T). By Equation (245) above, it is clear that each separate factor of T involves all orders of $\tilde{T}$ and vice versa:

$$[1 - ik\pi\tilde{T}|k\rangle\langle k|]T = \tilde{T} \quad (262)$$

so that $$T = [1 - ik\pi\tilde{T}|k\rangle\langle k|]^{-1} \tilde{T} \quad (263)$$

$$= \sum_{n=1}^{\infty} (-ik\pi\tilde{T}|k\rangle\langle k|)^n \tilde{T} \quad (264)$$

Thus it is clear that $\tilde{V}_j$ and $V_j$ cannot be the same.

Now we ask how can one combine measured data with the Volterra inverse series? We compute the back-scattering matrix element of Equation (250):

$$<-k|\tilde{T}|k>=\tilde{T}(-k,k)=<-k|\tilde{V}_1|k>=\tilde{V}_1(-k,k) \quad (265)$$

But $\tilde{T}(-k,k)$ is not directly measured. The far-field quantities typically measured are $r(k)=-ik\rho(-k,k)$, the reflection amplitude, and $t(k)=1-ik\pi T(k,k)$, the transmission amplitude. By Equation (245), we write $$T(-k,k)=\tilde{T}(-k,k)-ik\pi\tilde{T}(-k,k)T(k,k) \quad (266)$$

so $$\tilde{V}_1(-k, k) = \frac{ir(k)}{k\pi t(k)} \quad (267)$$

This expression is inverse-Fourier transformed to the space-domain, yielding $\tilde{V}_1(z)$. The result is $$\tilde{V}_1(z) = \frac{2i}{\pi}\int_{-\infty}^{+\infty}dk\frac{e^{-2ikz}r(k)}{kt(k)} = -\frac{4}{\pi}\int_0^{+\infty}dk\frac{1}{k}\text{Im}\frac{e^{-2ikz}r(k)}{t(k)} \quad (268)$$

One obtains the higher order $\tilde{V}_j(z)$ according to $$\tilde{V}_j(z) = \int_{-\infty}^{+\infty}d(2k)e^{-2ikz}\langle-k|\tilde{V}_{j-1}\tilde{G}_{0k}\tilde{V}_1|k\rangle \quad (269)$$

$$= \frac{1}{2\pi}\int_{-\infty}^{+\infty}d(2k)e^{-2ikz}\int_{-\infty}^{+\infty}dz' \quad (270)$$

$$\int_{-\infty}^{+\infty}dz''e^{ikz(z'+z'')}\tilde{V}_{j-1}(z')\tilde{G}_{0k}(z',z'')\tilde{V}_1(z'')$$

Again, it is instructive to carry out the application to scattering by the Dirac delta function interaction discussed earlier. In that case, we have $$r(k) = \frac{-ik\gamma}{2+ik\gamma}e^{2ikz_0} \quad (271)$$

$$t(k) = \frac{2}{(2+ik\gamma)} \quad (272)$$

It can then be shown that $$\tilde{V}_1(z)=\gamma\delta(z-z_0) \quad (273)$$

The second order corrections is given by $$\tilde{V}_2(z) = \gamma^2\int_{-\infty}^{+\infty}d(2k)e^{-2ikz}\int_{-\infty}^{+\infty}dz' \quad (274)$$

$$\int_{-\infty}^{+\infty}dz''e^{ikz(z'+z'')}\delta(z'-z_0)\tilde{G}_{0k}(z',z'')\delta(z''-z_0)$$

$$= \gamma^2\int_{-\infty}^{+\infty}d(2k)e^{-2iikz}\tilde{G}_{0k}(z_0,z_0) \equiv 0 \quad (275)$$

It should be clear that all $\tilde{V}_j$ vanish for $j\geq 2$. We conclude that the Volterra inverse scattering series converges to the exact answer in a single term, in the same manner as the forward Volterra series for the Dirac delta function interaction. We note that a crucial change from the Born-Neumann approach to the Lippmann-Schwinger-based inversion is that now, we require both $r(k)$ and $t(k)$ to use the Volterra inverse series!

Before leaving this example, we point out that Razavy [4C] has considered the interaction $2\lambda\delta(x)$ within the Lippmann-Schwinger-based inverse scattering series. Again, analytical results are obtained and the exact result is equal to the sum of the $V_1$ and $V_2$ terms. However, the higher order terms were not evaluated, they do not vanish, and involve alternating signs. Thus, it appears that the series is only conditionally convergent, depending on the order in which the terms are grouped and summed.

E. The Volterra Series for Non-Local Potentials

Up to this point, we have established that the Volterra property is shared by the coordinate representation matrix element, $<z|\tilde{T}|z'>$, if the interaction is local. In fact, we now show that this result is true for all non-local interactions so long as they also possess the Volterra kernel property. We recall that the exact solution for T is $$\tilde{T}=\gamma V+\gamma^2 V\tilde{G}V \quad (276)$$

where $$\tilde{G}=\tilde{G}_0+\tilde{G}_0\gamma V\tilde{G} \quad (277)$$

and $$\tilde{G}(z,z')=0, \quad z\geq z' \quad (278)$$

Now we do not restrict V to be local but we require that $$V(z,z')=0, \quad z>z' \quad (279)$$

We want to prove that it remains true that $\tilde{T}(z,z')=0$, $z>z'$. Our equation now is $$\tilde{T}(z, z') = \quad (280)$$

$$\gamma V(z, z') + \gamma^2 \int_z^{+\infty}dz''\int_{-\infty}^{z'}dz'''V(z, z'')\tilde{G}(z'', z''')V(z''', z')$$

where we use the facts that $z''$ must be greater than $z$ and $z'$ must be greater than $z'''$, due to the presence of the factors $V(z, z'')$ and $V(z''', z')$. Now suppose that $z>z'$. The first term on the RHS of Equation (280) vanishes for this condition. But the second term only has non zero contributions for $z'>z'''>z''>z$ since all terms involving $z''>z'''$ vanish due to the factor $\tilde{G}(z'', z''')$. Therefore, the only nonzero terms contradict the condition $z>z'$. We conclude that $\tilde{T}(z, z')=0$ if $z>z'$, if the non-local potential has the same property.

The analysis that the kernel of the inverse scattering equation has the Volterra property and, therefore, a Fredholm determinant that equals one can be carried out and we do not write it explicitly here. If one has the most general form of non-local potential, $V(z, z')$, for 1D scattering, then it turns out that the inversion requires measuring both the far and near fields. Clearly, the operator equations obtained from the inversion of $k^2\gamma V$ in terms of the $\tilde{V}_j$'s hold regardless of whether the potential is local or non-local. This is also true of the absolute convergence of the series for $k^2\gamma V$ in terms of the $\tilde{V}_j$ (provided V itself has a Volterra-kernel structure). However, if the non-local potential has the general form $V(z,z')$, then Equation (250) becomes $$\tilde{T}(k',k)=\tilde{V}(k',k) \quad (281)$$

with k' and k independent of one another. Then one uses Equation (245) to determine the off-shell elements of $\tilde{T}$ in terms of the physical T-matrix elements:

$$T(k',k) = \tilde{T}(k',k) - ik\pi \tilde{T}(k',k) T(k,k) \tag{282}$$

so that $$\tilde{T}(k', k) = \frac{T(k', k)}{1 - ik\pi T(k, k)} \tag{283}$$

Thus, knowledge of the on- and half-off-shell T-matrix elements enables one to determine the corresponding elements of the $\tilde{T}$-matrix. Then inverse Fourier transforming on both k' and k independently yields $\tilde{V}_1(z,z')$, which enables one to determine all higher $\tilde{V}_j(z,z')$, j>1.

It should be clear that scattering interactions that can be expressed in the form $$V(z)\frac{d^n}{dz^n}\delta(z-z')$$

will also produce Volterra kernels (that is, interactions involving derivatives of the field). Thus, the range of systems for which our results hold is very broad.

XV. Application to the Square Well or Barrier

As a second example, we present the results of the Volterra-based inverse series for acoustic scattering by a finite width well or barrier. Again the reflection and transmission amplitudes can be obtained analytically, as can the various $\tilde{V}_j$ terms in the power series for the potential. One can show that $$r(k) = \frac{V_0}{(2-V_0) + 2i\sqrt{1-V_0}\cot(ak\sqrt{1-V_0})} \tag{284}$$

$$t(k) = \frac{2\sqrt{1-V_0}\, ie^{-ika}}{V_0 \sin(ak\sqrt{1-V_0})} r(k) \tag{285}$$

In the case of $V_0<0$, one can have any finite value for the magnitude of the interaction (corresponding to any finite increase in the velocity of sound in the medium). In the case of a barrier, $0<V_0<1$; otherwise one encounters an infinite ($V_0=1$) or pure imaginary ($V_0>1$) velocity of sound. It follows that $$\tilde{V}_1(2k) = \frac{V_0}{2\pi k\sqrt{1-V_0}} \sin(ak\sqrt{1-V_0}) e^{ika} \tag{286}$$

The $\tilde{V}_1(z)$ is then $$\tilde{V}_1(z) = \frac{V_0}{\pi\sqrt{1-V_0}} \int_{-\infty}^{+\infty} dk \frac{\sin(ak\sqrt{1-V_0})}{k} e^{ik(a-2z)} \tag{287}$$

which is recognized as the Fourier transform of the sinc-function. This is well known to be a square well or barrier:

$$\tilde{V}_1 = \frac{V_0}{\sqrt{1-V_0}}, \; |a-2z| < a\sqrt{1-V_0} \tag{288}$$

$$= 0, \text{ all other } z \tag{289}$$

Rearranging, we find that the region where $\tilde{V}_1$ is nonzero is $$z_{min} < z < z_{max} \tag{290}$$

$$z_{min} = \frac{a}{2}(1 - \sqrt{1-V_0}) \tag{291}$$

$$z_{max} = \frac{a}{2}(1 + \sqrt{1-V_0}) \tag{292}$$

For a barrier, $0<V_0<1$ and the first order result has a higher barrier than the true one. For a well, $V_0<0$ and the first order result is shallower than the true one. Thus, although the first order result has the correct analytical form of a square well or barrier, it has in correct width and height (or depth). However, the explicit form of the result is such that it is trivial to obtain the exact potential from $z_{min}$ and $z_{max}$. It can be seen that $$V_0 = 1 - \left(\frac{z_{max} - z_{min}}{z_{max} + z_{min}}\right)^2 \tag{293}$$

and $$a = z_{max} + z_{min} \tag{294}$$

$$a = \frac{2z_{min}}{1 - \sqrt{1-V_0}} = \frac{2z_{max}}{1 + \sqrt{1-V_0}} \tag{295}$$

These exact, analytical expressions are found to work very well in computational studies as well. Thus, it is not necessary to evaluate the $\tilde{V}_j$ beyond j=1 in order to obtain the exact parameters for a square well or barrier interaction. Even so, these higher order terms an also be evaluated analytically.

These results can again be compared to those obtained using the Fredholm-based Born-Neumann inverse scattering series. Razavy [4C] has also obtained an expression for the $V_1$ term. In fact, the result is of the form of an infinite series, so a closed expression has not been possible. This also prevented him from obtaining higher order corrections. However, the structure manifested at the first order is not a simple square well but rather an infinite sequence of steps of decreasing magnitude. Razavy does not consider the convergence of the series. Despite these qualitatively incorrect features, it is never-the-less possible to use Razavy's result to determine the square interaction parameters exactly. This is because the terms in the infinite series permit one to obtain the correct $V_0$ and $\alpha$-parameter from the first of the infinite series of steps. However, because the Fredholm-based inversion produces unphysical artifacts that are absent from the Volterra-based results, the latter provides a more robust framework for an inversion when one has an interaction that does not yield an explicit formula for the various terms in the series.

It is remarkable that the Volterra-based inverse scattering series for both of these simple potentials is able to provide either the exact answer or the exact functional form of the interaction with only the first order term. Furthermore, the fat that all higher order terms can be evaluated analytically is very useful. We stress that these results are consequences of the fact that the Volterra-based inversion makes use of both the reflection and transmission information.

XVI. Conclusions and Future Work

In this portion of the application, we have used the fat that the acoustic scattering Lippmann-Schwinger integral equation (in 1D) involving the causal (or anti-causal) Green's function can be renomialized to write it as a Volterra integral equation. Such equations possess the best possible convergence behavior under Born-Neumann iteration. Furthermore, for a wide class of interactions (local, differential, or non-local but with the Volterra property), the auxiliary transition operator also possesses the Volterra property. Consequently, the inverse acoustic scattering series obtained by reverting the Volterra-based series in terms of $\tilde{V}_j$ also converges absolutely and uniformly for all $|\gamma|<\infty$. This does not, of course, ensure that the rate of convergence is conveniently rapid. It is well-known that an absolutely convergent series can be rearranged or grouped in any manner without affecting its convergence [Kaplan [16C]]. Of course, this is not true for divergent or conditionally convergent series. In the case of seismic scattering, one may expect the changes in the velocity of sound to be modeled reasonably by piece-wise constant interactions sine the distance over which there can be large changes should be small compared to distances over which the sonic speed changes less rapidly.

Our results show that a Volterra-based inversion can be done as a single comprehensive task, provided one has both the reflection and transmission amplitudes as functions of k. Indeed, all 1D scattering problems that can be formulated in a Lippmann-Schwinger framework have now been shown to be invertible, given the r(k) and t(k). In subsequent work we shall consider this approach for scattering in higher dimensions as well. The implications for various applications such as medial imaging, seismic exploration, non-destructive testing, etc. are undercurrent study and results will be reported as they are obtained.

By appropriate use of Equation (194), we have been able to express the Volterra-based inversion in a form that requires only r(k) as input, rather than both r(k) and t(k). This is an important reduction in the experimental data required to apply our approach. It has been pointed out to us that for the Dirac delta interaction, an approach based on the Heitler damping relation also yields the exact result [17C]. The approach is for evaluating a first order approximation only. A complete discussion of the relation to the present approach will be given elsewhere.

Appendix C

In this Appendix we give a few more details regarding the Fredholm solution of Equation (28), $$p_k(z) = e^{ikz} + \int_z^{+\infty} dz'' k^2 \gamma K(z, z'') p_k(z'') \tag{296}$$

where K(z, z'') is defined in Equations (201)–(202). The solution may be written as $$p_k = e^{ikz} + \int_0^{+\infty} dz' \frac{D(z, z')}{D} e^{ikz'} \tag{297}$$

where $$D = 1 - k^2 \gamma \int_0^{+\infty} dz K(z, z) + \tag{298}$$
$$\frac{(k^2\gamma)^2}{2!} \int_0^{+\infty} dz \int_0^{+\infty} dz' \det\begin{pmatrix} K(z,z) & K(z,z') \\ K(z',z) & K(z',z') \end{pmatrix} - \cdots$$

and $$D(z, z') = k^2 \gamma K(z, z') - \tag{299}$$
$$(k^2\gamma)^2 \int_0^{+\infty} dz'' \det\begin{pmatrix} K(z,z') & K(z,z'') \\ K(z'',z') & K(z'',z'') \end{pmatrix} + \cdots$$

Note that K(z,z) vanishes so long as V(z) is not too singular. Therefore, all diagonal terms in the determinants appearing in Equation (298) for D vanish. All other terms vanish, as discussed in the text above, sine they are of the form $\text{Tr}(K^n)$. Consequently, D=1. Now consider the integral $$\int_0^\infty dz' D(z, z') e^{ikz'}.$$

We assume, for simplicity and convenience, that the potential has compact support on the domain [0, Z], and that it is bounded. For any value of k and $\gamma$, we conclude that $k^2\gamma K(z, z')<|a|$, where a is some finite number. By Hadamard's theorem [6, 14], the value of an nth order determinant formed from such elements is bounded by $|a|^n n^{n/2}$. Then the nth term, say $t_n$, in Equation (299) is bounded by $$t_n < \frac{1}{n!} Z^n |a|^n n^{n/2} \tag{300}$$

Using Stirling's approximation, one has that $$t_n < \frac{Z^n |a|^n}{e^{-n} n^{n/2} n^{1/2}} \tag{301}$$

By the root test (Kaplan [16]), we see that $$\lim_{n\to\infty} (t_n)^{1/n} = \lim_{n\to\infty} \left(\frac{Z|a|e}{n^{1/2} n^{1/2n}}\right) = 0 \tag{302}$$

The radius of convergence is one divided by this limit so we conclude that the series for D (z, z') converges absolutely independent of the strength of the coupling parameter, $\gamma$ or the value of k.

The most robust treatment of the inverse acoustic scattering problem is that based on the reversion of the Born-Neumann series solution of the Lippmann-Schwinger equation. An important issue for this approach to inversion is the radius of convergence of the Born-Neumann series for Fredholm integral kernels, and especially for acoustic scattering for which the interaction depends on the square of the frequency. By contrast, it is well known that the Born-Neumann series for the Volterra integral equations in quantum scattering are absolutely convergent, in-dependent of the strength of the coupling characterizing the interaction. The transformation of the Lippmann-Schwinger equation from a Fredholm to a Volterra structure by renormalization has been considered previously for quantum scattering calculations and electromagnetic scattering. In this portion of the application, we employ the renormalization technique to obtain a Volterra equation framework for the inverse acoustic scattering series, proving that this series also converges absolutely in the entire complex plane of coupling constant and frequency values. The present results are for acoustic scattering in one dimension but the method is general. The approach is illustrated by applications to two simple one dimensional models for acoustic scattering.

REFERENCES

[1C] A. B. Weglein, K. H. Matson, D. J. Foster, P. M. Carvalho, D. Corrigan, S. A. Shaw, Imaging and inversion at depth without a velocity model: theory, concepts and initial evaluation, So. Exploration Geophysics 2000, Expanded Abstracts, Calgary, Calif.; A. B. Weglein and R. H. Stolt, Migration-inversion revisited, in The Leading Edge (1999) 950. See also the subseries approach to removing multiples from seismic data in A. B. Weglein, F. A. Gasparotto, P. M. Carvalho, and R. H. Stolt, Geophysics 62, 1775 (1997).

[2C] R. Jost and W. Kohn, Phys. Rev. 87, 977 (1952).

[3C] H. E. Moses, Phys. Rev. 102, 559 (1956).

[4C] M. Razavy, J. Acoust. So. Am. 58, 956 (1975).

[5C] P. M. Morse and H. Feshbah, Methods of Theoretical Physics (McGraw-Hill, New York, 1953).

[6C] R. G. Newton, Scattering Theory of Waves and Particles (Springer-Verlag, New York, 1982).

[7C] M. L. Goldberger and K. M. Watson, Collision Theory (Wiley, New York, 1964).

[8C] R. T. Prosser, J. Math. Phys. 10, 1819 (1969); ibid., 17, 1775 (1976); ibid. 21, 2648 (1980).

[9C] R. Courant and D. Hilbert, Methods of Mathematical Physics (Interscience, New York, 1953).

[10C] W. N. Sams and D. J. Kouri, J. Chem. Phys. 51, 4809 and 4815 (1969).

[11C] D. J. Kouri, J. Math. Phys. 14, 1116 (1973).

[12C] To be published.

[13C] A. B. Weglein, private communication.

[14C] L. S. Rodberg and R. M. Thaler, The Quantum Theory of Scattering (Academic Press, New York, 1967).

[15C] J. Mathews and R. L. Walker, Mathematical Methods of Physics (Benjamin, New York, 1965).

[16C] W. Kaplan, Advanced Calculus (Addison-Wesley, Reading, Mass., 1952).

[17C] A. J. Devaney and A. B. Weglein, J. Inverse Problems 5, 49 (1989).

3D Acoustic Spherical Interaction and Non-Spherical Interaction

The following equation is the general acoustic case:

$$kr\left[P_{lik}^+(r) = j_l(kr) - \frac{2mk}{\hbar^2}\int_0^\infty dr' r'^2 h_l^+(kr_>)j_l(kr_<)k^2 V(r')P_{lik}^+(r')\right] \quad (303)$$

Introduction—Ricetti Functions

Let $$H_l^+ = krh_l^+$$

and $J_l = krj_l$ for $m = \frac{1}{2}$ and $\hbar = 1$ for the acoustic case.

$$P_{lik}^+(r) = \quad (304)$$
$$krP_{lk}^+ = J_l(kr) - k\int_0^\infty dr' H_l^+(kr_>)J_l(kr_<)V(r')P_{lik}^+(r')$$

$$P_{lik}^+(r) = J_l(kr)\left[1 - k\int_0^\infty dr' H_l^+(kr)V(r')P_{lik}^+(r')\right] - \quad (305)$$
$$k\int_0^r dr' [N_l(kr)J_l(kr') - J_l(kr)N_l(kr')]V(r')P_{lik}^+(r')$$

where $H_l^+ = N_l + iJ_l$. Then $T_l|J_{lk}\rangle = VP_{lk}^+(r)$ $$T_l = V + VG_{10k}^+ T_l \quad (306)$$

$$G_{10k}^+ = -kH_l^+(kr_>)J_l(kr_<) \quad (307)$$

$$G_{10k}^+ = \tilde{G}_{10k} - k|J_{lk}\rangle\langle H_{lk}^+| \quad (308)$$

$$T_l = V[1 - k|J_{lk}\rangle\langle H_{lk}^+|T_l] + V\tilde{G}_{10k}T_l \quad (309)$$

so that we can derive the following $$T_l = T_l[1 - k|J_{lk}\rangle\langle H_{lk}^+|T_l] \quad (310)$$

$$\tilde{T}_l = V + V\tilde{G}_{10k}\tilde{T}_l \quad (311)$$

$$V = \sum_j \tilde{V}_j, \; \tilde{V}_1 = \tilde{T}_l, \; \tilde{V}_j = \tilde{V}_{j-1}\tilde{G}_{10k}\tilde{V}_1, \; j \geq 2 \quad (312)$$

$$P_{\vec{k}}^+(\vec{r}) = 4\pi\sum_{l\mu} i^l Y_{l\mu}^*(\hat{k})Y_{l\mu}(\hat{r})P_{lk}^+(r) \quad (313)$$
$$= \frac{4\pi}{kr}\sum_{l\mu} i^l Y_{l\mu}^*(\hat{k})Y_{l\mu}(\hat{r})P_{lk}^+(r)$$

$$\left[P_{\vec{k}}^+ - e^{i\vec{k}\cdot\vec{r}}\right] = P_{\vec{k},sw}^+(\vec{r}) \quad (314)$$

where $$P_{\vec{k},sw}^+(\vec{r})$$

is data from spectra.

At r outside the range of V(r), we have:

$$P^+_{\vec{k},sw}(\vec{r}) = -\frac{4\pi}{r}\sum_{l\mu} i^l H^+_l(kr) Y^*_{l\mu}(\hat{k}) Y_{l\mu}(\hat{r}) \int_0^R dr' J_l(kr') V(kr') P^+_{lk}(r') \quad (315)$$

We now define:

$$T^{(1)}_l = \int_0^R dr' J_l(kr') V(r') P^+_{lk}(r') = \langle J_{lk} | T_l | J_{lk} \rangle \quad (316)$$

$$\text{Data} = -\frac{4\pi}{r}\sum_l (2l+1) P_l(\vec{k}\cdot\vec{r}) H^+_l(kr) T^{(1)}_l \quad (317)$$

$$T^{(1)}_l = \tilde{T}^{(1)}_l [1 - k T^{(2)}_l] \quad (318)$$

where $$T^{(2)}_l \equiv \langle H^+_{lk} | T_l | J_{lk} \rangle \quad (319)$$

and $$T^{(2)}_l = \tilde{T}^{(2)}_l [1 - k T^{(2)}_l] \quad (320)$$

$$T^{(2)}_l = \frac{\tilde{T}^{(2)}_l}{1 + k \tilde{T}^{(2)}_l} \quad (321)$$

which yields $$T^{(1)}_l = \tilde{T}^{(1)}_l \left[ 1 - \frac{k\tilde{T}^{(2)}_l}{1 + k\tilde{T}^{(2)}_l} \right] = \frac{\tilde{T}^{(1)}_l}{1 + k\tilde{T}^{(2)}_l} \quad (322)$$

$$\text{Data} = -\frac{4\pi}{r}\sum_l (2l+1) P_l(\vec{k}\cdot\vec{r}) H^+_l(kr) \frac{\tilde{T}^{(2)}_l}{(1 + k\tilde{T}^{(2)}_l)} \quad (323)$$

Then to first order, $\tilde{V}_1 = \tilde{T}_l$, so that $$\text{Data} = -\frac{4\pi}{r}\sum_l (2l+1) P_l(\vec{k}\cdot\vec{r}) H^+_l(kr) \frac{\tilde{V}^{(1)}_{1l}}{(1 + k\tilde{V}^{(2)}_{1l})} \quad (324)$$

where $$\tilde{V}^{(1)}_{1l} = \langle J_{lk} | \tilde{V}_1 | J_{lk} \rangle \quad (325)$$

$$\tilde{V}^{(2)}_{1l} \equiv \langle H^+_{lk} | \tilde{V}_1 | J_{lk} \rangle \quad (326)$$

The higher order corrections are given by:

$$\tilde{V}_2(r) = \left(-\tilde{V}_1 \tilde{G}_{l0k} \tilde{V}_1\right)_r \quad (327a\ldots)$$

$$\vdots$$

$$\tilde{V}_j(r) = \left(-\tilde{V}_{j-1} \tilde{G}_{l0k} \tilde{V}_1\right)_r$$

The higher order corrections converge absolutely and uniformly allowing analysis of inverse scattering spectral data to any level of accuracy.

Additional Notation for the Non-Spherical Case $$kr[P^+(l\mu | l'\mu' | r)] = \delta_{ll'}\delta_{\mu\mu'} j_l(kr) - \quad (328)$$

$$\frac{2mk}{\hbar^2} \sum_{l''\mu''} \int d\vec{r}' Y^*_{l\mu}(\hat{r}') h^+_l(kr_>)$$

$$j_l(kr_<) k^2 V(\hat{r}') Y_{l''\mu''}(\hat{r}') P^+(l''\mu'' | l'\mu' | r')$$

$$(|J_k\rangle\langle H^+_k|)_{l\mu l'\mu'} = \delta_{ll'}\delta_{\mu\mu'} |J_{lk}\rangle\langle H^+_{lk}| \quad (329)$$

$$P'_k(l\mu|l'\mu'|r) = \delta_{ll'}\delta_{\mu\mu'} J_l(kr) - \quad (330)$$

$$k \sum_{l''\mu''} \int_0^\infty dr' r'^2 H^+_l(kr_>) J_l(kr_<)$$

$$V(l\mu|l''\mu''|r') P^+_k(l''\mu''|l'\mu'|r')$$

$$T(l\mu|l'\mu')|J_{l'k}\rangle = \sum_{l''\mu''} V(l\mu|l''\mu'')|P^+_k(l''\mu''|l'\mu')\rangle \quad (331)$$

$$\underline{VP}^+_k = \underline{TJ}_k \quad (332a\text{-}c)$$
$$\underline{P}^+_k(l'\mu') = \underline{J}_k(l'\mu') - k\underline{G}^+_{0k}\underline{VP}^+_k(l'\mu')$$
$$\underline{T} = \underline{V} + \underline{VG}^+_{0k}\underline{T}$$

diagonal matrix elements are given by:

$$\underline{T} = \underline{\tilde{T}}\left[\underline{1} - k\sum_{l\mu} |J_k(l\mu)\rangle\langle H^+_k(l\mu)|\underline{T}\right] \quad (333a\text{-}b)$$

$$\underline{\tilde{T}} = \underline{V} + \underline{V}\tilde{\underline{G}}_{0k}\underline{\tilde{T}}$$

$$\sum_{l''\mu''} V(l\mu|l''\mu''|r) P^+_k(l''\mu''|l'\mu'|r) = \quad (334a\text{-}c)$$

$$\sum_{l''\mu''} T(l''\mu''|l'\mu') \delta_{l''l'}\delta_{\mu''\mu'} J_{l'k}$$

$$\langle J_k(l\mu)|\underline{T}|J_k(l'\mu')\rangle = \langle J_k|\underline{\tilde{T}}|J_k\rangle$$
$$\langle J_k(l\mu)|\underline{T}|J_k(l'\mu')\rangle = T(l\mu|l'\mu')$$

We need to use the expression $$G^+_{0k} = \tilde{G}_{0k} + O$$

$$-\frac{1}{4\pi} \frac{e^{ik|\vec{r}-\vec{r}'|}}{|\vec{r}-\vec{r}'|} = -k \sum_{l\mu} Y_{l\mu}(\hat{r}) Y^*_{l\mu}(\hat{r}')^* [n_l(kr) j_l(kr') - \quad (335)$$

$$j_l(kr) n_l(kr')] -$$

$$k \sum_{l\mu} Y_{l\mu}(\hat{r}) Y^*_{l\mu}(\hat{r}')^* j_l(kr) h^+_l(kr')$$

-continued $$\tilde{G}_{0k} = -k \sum_{l\mu} [|Y_{l\mu}n_{lk}\rangle\langle Y_{l\mu}j_{lk}| - |Y_{l\mu}j_{lk}\rangle\langle Y_{l\mu}n_{lk}|] \quad (336\text{a-b})$$

$$O = -k \sum_{l\mu} |Y_{l\mu}j_{lk}\rangle\langle Y_{l\mu}h_{lk}^+|$$

$$T = V + V\tilde{G}_{0k}^+ T \quad (337\text{a-c})$$
$$= V + V\tilde{G}_{0k}T + VOT$$
$$= V[1 + OT] + V\tilde{G}_{0k}T$$

$$T = \tilde{T}[1 + OT]$$
$$\tilde{T} = V + V\tilde{G}_{0k}\tilde{T}$$

$$T^{(1)}(l\mu|l'\mu'|k) = \tilde{T}^{(1)}(l\mu|l'\mu'|k) + \langle Y_{l\mu}j_{lk}|\tilde{T}OT|Y_{l'\mu'}j_{l'k}\rangle \quad (338)$$
$$= \tilde{T}^{(1)}(l\mu|l'\mu'|k) - k \sum_{l''\mu''} \tilde{T}^{(1)}(l\mu|l''\mu''|k)$$
$$\tilde{T}^{(2)}(l''\mu''|l'\mu'|k)$$

$$T^{(2)}(l\mu|l'\mu'|k) = \tilde{T}^{(2)}(l\mu|l'\mu'|k) - \quad (339)$$
$$k \sum_{l''\mu''} \tilde{T}^{(2)}(l\mu|l''\mu''|k)\tilde{T}^{(2)}(l''\mu''|l'\mu'|k)$$

Solving for $T^{(2)}$ and plugging into equation (339) for $T^{(1)}$ ($l\mu|l'\mu'|k$). Then we take a first order treatment and higher order terms again result from $$\tilde{V}_j = -\tilde{V}_{j-1}\tilde{G}_{0k}\tilde{V}_1 \quad (340)$$

where $\tilde{G}_{0k}$ is as described previously leading to a data construction shown below:

$$f(\vec{k}\cdot\vec{r}) = \sum_{l\mu}\sum_{l'\mu'} Y_{l\mu}^*(\hat{k})Y_{l'\mu'}(\hat{r})T(l'\mu'|l\mu|k) \quad (341)$$

Now we can solve the case to the first order where $\tilde{T}=\tilde{V}_1$, implies $$\tilde{T}^{(2)}(l\mu|l'\mu'|k) = \langle Y_{l\mu}h_{lk}^+|\tilde{V}_1(\vec{r})|Y_{l'\mu'}j_{lk}\rangle \quad (342)$$
$$= \int d\vec{r} Y_{l\mu}^*(\hat{r})h_l^+(kr)\tilde{V}_1(\vec{r})Y_{l'\mu'}(\hat{r})j_l(kr)$$

$$T^{(2)}(l\mu|l'\mu'|k) = \tilde{V}_1^{(2)}(l\mu|l'\mu'|k) - \quad (343)$$
$$k \sum_{l''\mu''} \tilde{V}_1^{(2)}(l\mu|l''\mu''|k)\tilde{T}(l''\mu''|l'\mu'|k)$$

Now $$\tilde{V}_1^{(2)}(l\mu|l'\mu'|k)$$

can be expressed in terms of a set of calculable coefficients with a smaller number of unknown and therefore, reduced computational expense for achieving a given degree of accuracy in the calculated data verses the actual data. Thus, we can write:

$$\tilde{V}_1(\vec{r}) = \sum_{\bar{l}\bar{\mu}} Y_{\bar{l}\bar{\mu}} \tilde{V}_1(\bar{l}\bar{\mu}|r) \quad (344)$$

Get Clebsch-Gordan coefficients and a subset of basic integrals, which give rise to a formal description of $\underline{T}^{(1)}(k)$ as follows:

$$\underline{T}^{(1)}(k) = \underline{\tilde{T}}^{(1)}(k) - k\underline{\tilde{T}}^{(1)}(k)\underline{\tilde{T}}^{(2)}(k)$$

$$\underline{T}^{(2)}(k) = \underline{\tilde{T}}^{(2)}(k) - k\underline{\tilde{T}}^{(2)}(k)\underline{\tilde{T}}^{(2)}(k)$$

$$\underline{T}^{(2)}(k) = [\underline{1} + k\underline{\tilde{K}}^{(2)}(k)]^{-1}\underline{\tilde{T}}^{(2)}$$

$$\underline{T}^{(1)}(k) = \underline{\tilde{T}}^{(1)}(k)\left[\underline{1} - k\left[\underline{1} + k\underline{\tilde{T}}^{(2)}(k)\right]^{-1}\underline{\tilde{T}}^{(2)}(k)\right] \quad (345\text{a-d})$$
$$= \underline{\tilde{T}}^{(1)}(k)\left[\underline{1} + k\underline{\tilde{T}}^{(2)}(k)\right]^{-1}$$

We can now define $$\underline{V}^{(j)}(k) = \underline{T}^{(j)}(k) \quad (346)$$

and we get $$\underline{T}^{(1)}(k) = \underline{\tilde{V}}^{(1)}(k)[\underline{1} + k\underline{\tilde{V}}^{(2)}(k)]^{-1} \quad (347)$$

This give us $$T^{(1)}(l\mu|l'\mu'|k) = \sum_{l''\mu''} \tilde{V}^{(1)}(l\mu|l''\mu''|k)\left\{\left[\underline{1} + k\underline{\tilde{V}}^{(2)}(k)\right]^{-1}\right\}_{l\mu,l''\mu''} \quad (348)$$

This expression then is used in the expression for the scatted pressure wave. One determines $\tilde{V}_1(\vec{r})$. Then by using the full 3D $\tilde{G}_{0k}$ operator in the coordinate representation, we obtain the higher order corrections. They will be easier to determine because of their form than to calculate or determine $\tilde{V}_1(\vec{r})$. These equations have utility in ultrasound medical imaging and in sonar for submarines and ships to remove reverberations and sonic clutter.

Electromagnetic Inverse Scattering $$\varepsilon_{JM,J'M'}^{\lambda\lambda'}(r) = u_J(kr)\delta_{JJ'}\delta_{MM'}\delta_{\lambda\lambda'} + \quad (349)$$
$$\sum_{J''M''\lambda'''\lambda''} \int_0^\infty dr' \Gamma_{\lambda\lambda'''}^{J+}(r,r')\eta_{JM,J''M''}^{\lambda'''\lambda''}(r')\varepsilon_{J''M'',J'M'}^{\lambda''\lambda'}(r')$$

$$\varepsilon(\vec{k},\nu\vec{r}) = \frac{4\pi}{kr} \sum_{JM\lambda J'M'\lambda'} \bar{Y}_{JM}^{(\lambda)}(\hat{r})\varepsilon_{JM,J'M'}^{\lambda\lambda'}(r)\bar{Y}_{J'M'}^{(\lambda')}(\hat{k})\cdot\vec{X}_\nu \quad (350)$$

$$\Gamma_{\lambda\lambda'''}^{J+}(r,r') = \tilde{\Gamma}_{\lambda\lambda'''}^{J}(r,r') + B_{1\lambda\lambda'''}^{J}(r)B_{2\lambda\lambda'''}^{J}(r') \quad (351)$$

For the case of $\lambda=e$ and $\lambda'''=e$, we have $$\tilde{\Gamma}_{\lambda\lambda'''}^{J}(r,r') = k^2(u_J'(kr')w_J^{(+)}(kr) - u_J'(kr)w_J^{(+)}(kr')), \quad (352)$$
$$r' \leq r = 0, r' > r$$

$$B_{1\lambda\lambda'''}^{J}(r)B_{2\lambda\lambda'''}^{J}(r') = k^2 u_J'(kr)w_J^{(+)}(kr') \quad (353)$$

For the case of $\lambda=M$ and $\lambda'''=M$, we have $$\Gamma_{MM}^J(r,r') = k^2(-u_J'(kr')w_J'^{(+)}(kr) + u_J'(kr)w_J'^{(+)}(kr')), \quad (354)$$

$$r' \le r = 0, r' > r$$

$$B_{1MM}^J(r)B_{2MM}^J(r') = -k^2 u_J'(kr)w_J'^{(+)}(kr') \quad (355)$$

For the case of $\lambda=0$ and $\lambda'''=0$, we have $$\Gamma_{00}^J(r,r') = -\frac{(J+1)}{rr'}(u_J(kr')w_J^{(+)}(kr) + u_J(kr)w_J^{(+)}(kr')), \quad (356)$$

$$r' \le r = 0, r' > r$$

$$B_{100}^J(r)B_{200}^J(r') = -\frac{(J+1)}{rr'}u_J(kr)w_J^{(+)}(kr') \quad (357)$$

and we have $$\Gamma_{t0}^J(r,r') = \quad (358)$$

$$\Gamma_{0t}^J(r,r') = -\frac{[J(J+1)]^{1/2}}{r'}\frac{\partial}{\partial r}[u_J(kr')w_J^{(+)}(kr) - u_J(kr)w_J^{(+)}(kr')],$$

$$r' \le r = 0, r' > r$$

$$B_{1t0}^J(r)B_{20t}^J(r') = -\frac{[J(J+1)]^{1/2}}{r'}\frac{\partial}{\partial r}[u_J(kr)w_J^{(+)}(kr')] \quad (359)$$

$$\varepsilon_{JM,J'M'}^{\lambda\lambda'}(r) = u_J(kr)\delta_{JJ'}\delta_{MM'}\delta_{\lambda\lambda'}(\delta_{\lambda 0}-1) + \quad (360)$$

$$\sum_{\substack{J''M''\\\lambda'''\lambda''}} B_{1\lambda\lambda'''}^J(r)\int_0^\infty dr' B_{2\lambda\lambda'''}^J(r')\eta_{JM,J''M''}^{\lambda'''\lambda''}(r')\varepsilon_{J''M'',J'M'}^{\lambda''\lambda'}(r') +$$

$$\sum_{\substack{J''M''\\\lambda'''\lambda''}}\int_0^r dr' \Gamma_{\lambda\lambda'''}^J(r,r')\eta_{JM,J''M''}^{\lambda'''\lambda''}(r')\varepsilon_{J''M'',J'M'}^{\lambda''\lambda'}(r')$$

$$\vec{\mathcal{E}}(r) = \vec{U}(kr)\cdot\vec{\Delta}_0 + \vec{U}(kr)\cdot\vec{G}_1 + \quad (361)$$

$$\int_0^r dr' \vec{K}(r,r')\vec{\mathcal{E}}(r') + \vec{U}(kr)\cdot\vec{G}_2$$

where $$[\vec{\mathcal{E}}(r)]_{\lambda,JM,\lambda'J'M'} = \varepsilon_{JM,J'M'}^{\lambda\lambda'}(r) \quad (362)$$

$$[\vec{U}(r)]_{i,j'} = u_J(kr)\delta_{JJ'}\delta_{MM'}\delta_{\lambda\lambda'} \quad (363)$$

$$[\vec{\Delta}_0]_{JJ'MM'\lambda\lambda'} = (\delta_{\lambda 0}-1)\delta_{JJ'}\delta_{MM'}\delta_{\lambda\lambda'} \quad (364)$$

Then we can show that $$\vec{\mathcal{E}}(r) = \vec{\mathcal{E}}_0(r)\cdot[\vec{\Delta}_0 + \vec{G}_1] + \vec{\mathcal{E}}(r')\cdot\vec{G}_2 \quad (365)$$

$$\vec{\mathcal{E}}_0(r) = \vec{U}(kr) + \int_0^r dr' \vec{K}(r,r')\cdot\vec{\mathcal{E}}_0(r') = \sum_{j=0}^\infty \vec{\mathcal{E}}_{0j}(r) \quad (366)$$

$$\vec{\mathcal{E}}_1(r) = \vec{U}(kr) + \int_0^r dr' \vec{K}(r,r')\cdot\vec{\mathcal{E}}_1(r') = \sum_{j=0}^\infty \vec{\mathcal{E}}_{1j}(r) \quad (367)$$

Now asymptotically, for $r>r_{max}$, the scattering amplitude is obtained from $\vec{\mathcal{E}}(r)$ Thus, one determines $$\eta_{JM,J'M'}^{(1)\lambda\lambda'}(r)$$

from the scattering. Then, one obtains $$\eta_{JM,J'M'}^{(1)\lambda\lambda'}(r)$$

from the spectra to start the iterative process.

Subtraction Technique Approach to the Inverse Scattering Problem

Let $$T=V+KT \quad (368)$$

where $$K = VG_{0k}^+ \quad (369)$$

$$G_{0k}^+ = O_{0k} + \tilde{G}_{0k} \quad (370)$$

so $K=K_1+K_2$, where $$K_1=VO_{0k} \quad (371)$$

$$K_2=V\tilde{G}_{0k} \quad (372)$$

We now define the following operators as follows:

$$\Gamma_1 = 1 + K_1\Gamma_1 \quad (373)$$

$$\Gamma_1 = (1+K_1)^{-1} \quad (374)$$

Then, we can show $$T=\Gamma_1 V + \Gamma_1 K_2 T = (1-V_{0k})^{-1}V(1+\tilde{G}_{0k}T) \quad (375)$$

So we define the effective potential $\tilde{V}$ as follows:

$$\tilde{V}=(1-VO_{0k})^{-1}V \quad (376)$$

It can be shown that $\tilde{V}$ is non-local even if $V$ is local. Therefore, we can show that $$T=\tilde{V}+\tilde{V}\tilde{G}_{0k}T \quad (377)$$

We now require that $\tilde{V}$ is local (and also that $V$ is local). Solving for $\tilde{V}$, we obtain $$\tilde{V}=T(1+\tilde{G}_{0k}T)^{-1} \quad (378)$$

Now we perform a power series expansion of the fraction as follows:

$$(1 + \tilde{G}_{0k}T)^{-1} = \sum_{n=0}^{\infty} (-\tilde{G}_{0k}T)^n \tag{379}$$

to obtain the following equation:

$$\tilde{V} = \sum_{n=0}^{\infty} T(-\tilde{G}_{0k}T)^n \tag{380}$$

$$\equiv \sum_{j=1}^{\infty} \lambda^j \tilde{V}_j \tag{381}$$

and T is first order in $\lambda$, so $$\sum_{j=1}^{\infty} \lambda^j \tilde{V}_j = \sum_{n=0}^{\infty} T(-\tilde{G}_{0k}T)^n \lambda^{n+1} \tag{382}$$

Then we can write $$\tilde{V}_1 = T \tag{383}$$

$$\tilde{V}_j = -\tilde{V}_{j-1} \tilde{G}_{ok} \tilde{V}_1 \tag{384}$$

Since $\tilde{V}_1$ must be local in coordinate space, it is completely determined by the matrix elements $<-\vec{k}|T|\vec{k}>$ (Newton, Scattering Theory of Waves and Particles, Springer-Verlag, New York, 1982, chpt. 20). Additionally, off-shell element of $\tilde{V}_1$ are easily gotten as $<\vec{k}'|\tilde{V}_1|\vec{k}>$ so $\tilde{V}$ can be constructed. The physical potential is obtained from equation (376):

$$(1 - VO_{0k})\tilde{V} = V \tag{385}$$

so $$\tilde{V} = V + VO_{ok}\tilde{V} \tag{386}$$

We can evaluate from $-k, k$ matrix elements to solve for $\tilde{V}(2k)$ and Fourier invert.

$$V = \tilde{V}(1 + O_{ok}\tilde{V})^{-1} \tag{387}$$

The fact that $\tilde{V}$ is local will ensure that V is also local, since $O_{0k}$ is a separable operator. This is an alternative way to obtain the same inversion as before. The only iteration is for the Volterra kernel equation $\tilde{V}$ or T of equation (377). We also note that $$T = \tilde{V} + \tilde{V}\tilde{G}_k \tilde{V} \tag{388}$$

The operator $\tilde{G}_k$ is Volterra so for V local, T is also Volterra.

Now evaluating the equations in momentum space, we have $$(1 - VO_{0k})\tilde{V} = V \tag{389}$$

$$(1 + ik\pi V|k><k|)\tilde{V} = V \tag{390}$$

$$\tilde{V}(2k) + ik\pi V(2k)\tilde{V}(0) = V(2k) \tag{391}$$

But if we set $k=0$, then we have $$\tilde{V}(0) = V(0) \tag{392}$$

that is the average of $\tilde{V}$ and V are the same. Therefore, we have $$\tilde{V}(2k) = V(2k)[1 - ik\pi V(0)] \tag{393}$$

from which $\tilde{V}(z)$ can be obtained by inverse Fourier transformation.

Alternatively, $$\tilde{V}(2k) + ik\pi V(2k)\tilde{V}(0) = V(2k) \tag{394}$$

$$V(2k) = \frac{\tilde{V}(2k)}{1 - ik\pi \tilde{V}(0)} \tag{395}$$

and this expression is correct since V(0) is essentially t(k).

Miscellaneous Volterra Inverse Scattering Results $$\frac{1}{E - K + i\varepsilon} = \tilde{G}_{0k} - \frac{i\pi}{k}|k\rangle\langle k| \tag{396}$$

so we now have $$\tilde{G}_{0k} = \frac{1}{E - K + i\varepsilon} + \frac{i\pi}{k}|k\rangle\langle k| \tag{397}$$

$$1 = \int_{-\infty}^{+\infty} dr'|k'\rangle\langle k'| \tag{398}$$

$$\delta(E - K) = \int_{-\infty}^{+\infty} dk' \delta(E - k'^2)|k'\rangle\langle k'| \tag{399}$$

$$E' = k'^2 \tag{400a-c}$$
$$dE' = 2k'dk'$$
$$dk' = \frac{1}{2\sqrt{E'}}dE'$$

$$\delta(E - K) = \int_0^{+\infty} dk' \delta(E - k'^2)|k'\rangle\langle k'| + \int_{-\infty}^0 dk' \delta(E - k'^2)|k'\rangle\langle k'| \tag{401}$$

Now let $-u=k'$ and $du=-k'$, then we can derive $$\delta(E - K) = \int_{-\infty}^{+\infty} du \delta(E - u^2)|-u\rangle\langle -u| \tag{402}$$

$$\delta(E - K) = \frac{1}{2k}[|k\rangle\langle k| + |-k\rangle\langle -k|] \tag{403}$$

$$-i\pi\delta(E - K) = -\frac{i\pi}{2k}[|k\rangle\langle k| + |-k\rangle\langle -k|] \tag{404}$$

Therefore, we can write $$\tilde{G}_{0k} = \frac{P}{E - K} + \frac{i\pi}{2k}[|k\rangle\langle k| - |-k\rangle\langle -k|] \tag{405}$$

The principle leading term is part of a Green's function.

General Approach to Volterra-Based Inversion
Quantum Scattering Case

We start with $$T = V + VG_{0k}^+ T \qquad (406)$$

$$G_{0k}^+ = -\frac{2mk}{\hbar^2} \sum_l \sum_m Y_{lm}(\hat{r})Y_{lm}(\hat{r}')^* h_l^+(kr_>)j_l(kr_<) \qquad (407)$$

We can now separate $$G_{0k}^+$$

into a Volterra kernel plus a separable Fredholm kernel:

$$G_{0k}^+ = \tilde{G}_{0k} + O_k \qquad (408)$$

$$O_k = -\frac{2mk}{\hbar^2} \sum_l \sum_m |Y_{lm}j_{lk}\rangle\langle Y_{lm}h_{lk}^+| \qquad (409)$$

where $$<\vec{r}|Y_{lm}j_{lk}> = Y_{lm}(\hat{r})j_l(kr) \qquad (410)$$

$$\langle \vec{r}'|Y_{lm}h_{lk}^+\rangle = Y_{lm}(\hat{r}')h_{lk}^+(kr') \qquad (411)$$

and with $$h_{lk}^+(kr) = n_l(kr) + ij_l(kr),$$

$$G_{0k}^+ = -\frac{2mk}{\hbar^2} \sum_l \sum_m [|Y_{lm}n_{lk}\rangle\langle Y_{lm}j_{lk}| - |Y_{lm}j_{lk}\rangle\langle Y_{lm}n_{lk}|], \qquad (412)$$
$$r' \leq r$$
$$= 0, r' > r \qquad (413)$$

Using equation (407) and equation (410), we can write $$T = V + VO_k T + V\tilde{G}_{0k}T \qquad (414)$$

We can now separate the Volterra and Fredholm pieces of equation (414) by defining $\tilde{T}$ by $$T = \tilde{T}[1 + O_k T] \qquad (415)$$

$$\tilde{T} = V + V\tilde{G}_{0k}\tilde{T} \qquad (416)$$

To generate V, we expand it in orders of $\tilde{T}$ and require the coefficient of each $\lambda^j$ vanish separately. Thus, $$V = \sum_{j=1}^\infty \lambda^j \tilde{V}_j \qquad (417)$$

and $$\tilde{T} \approx \lambda \tilde{T} \qquad (418)$$

Then by equation (12)

$$\lambda \tilde{T} = \sum_{j=1}^\infty \lambda^j \tilde{V}_j + \sum_{j=1}^\infty \lambda^j \tilde{V}_j G_{0k} \lambda \tilde{T} \qquad (419)$$

Therefore $$\tilde{V}_1 = \tilde{T} \qquad (420)$$

and $$\tilde{V}_j = -\tilde{V}_{j-1}\tilde{G}_{0k}\tilde{V}_1, j > 1 \qquad (421)$$

We shall assume that all backscattering elements of T are known, i.e., all elements of $<-\vec{k}|T|\vec{k}>$ are known. We now define a local operator $V_1(\vec{r})$ such that $$\langle -\vec{k}|T|\vec{k}\rangle \equiv \frac{1}{(2\pi)^3} \int d\vec{r}' e^{2i\vec{k}\cdot\vec{r}'} V_1(\vec{r}') \qquad (422)$$

If $<-\vec{k}|T|\vec{k}>$ is measured (known), then $V_1(\vec{r})$ results from the inverse Fourier transform as shown below:

$$2\int d\vec{k} e^{-2i\vec{k}\cdot\vec{r}} \langle -\vec{k}|T|\vec{k}\rangle = \frac{1}{(2\pi)^3}\int d(2\vec{k})\int d\vec{r}' e^{2i\vec{k}\cdot(\vec{r}'-\vec{r})} V_1(\vec{r}') \qquad (423)$$

which lead to the following:

$$V_1(\vec{r}) = 2\int d\vec{k} e^{-2i\vec{k}\cdot\vec{r}} \langle -\vec{k}|T|\vec{k}\rangle \qquad (424)$$

We note that once $V_1(\vec{r})$ is known, then we can compute its matrix elements in any other representation. To determine $\tilde{V}_1(\vec{r})$, we must solve the Fredholm integral equation set forth in equation (415). Using equation (410), we have $$V_1 = \tilde{V}_1\left[1 - \frac{2mk}{\hbar^2}\sum_l \sum_m |Y_{lm}j_{lk}\rangle\langle Y_{lm}h_{lk}^+|V_1\right] \qquad (425)$$

The general matrix element of v, and $\tilde{V}_1$, in the angular momentum, radial basis are given below:

$$<Y_{lm}j_{lk}|V_1|Y_{l'm'}j_{l'k}> = \int d\vec{r}\int d\vec{r}' Y_{lm}^*(\hat{r})j_{lk}(kr) V_1(\vec{r},\vec{r}')Y_{l'm'}(\hat{r}')j_{l'k}(kr') \qquad (426)$$

But we also have $$V_1(\vec{r}, \vec{r}\,') = \delta(\vec{r} - \vec{r}\,') V_1(\vec{r}) \quad (427)$$

leading to the following $$\langle Y_{lm} j_{lk} | V_1 | Y_{l'm'} j_{l'k} \rangle = \int d\vec{r}\, Y_{lm}^*(\hat{r}) j_{lk}(kr) V_1(\vec{r}) Y_{l'm'}(\hat{r}) j_{l'k}(kr) \quad (428)$$

The same is true for the $\tilde{V}_1$-matrix $$\langle Y_{lm} j_{lk} | \tilde{V}_1 | Y_{l'm'} j_{l'k} \rangle = \int d\vec{r}\,' Y_{lm}^*(\hat{r}) j_{lk}(kr) \tilde{V}_1(\vec{r}) Y_{l'm'}(\hat{r}') j_{l'k}(kr') \quad (429)$$

Then equation (425) yields $$\langle Y_{l''m''} j_{l''k} | V_1 | Y_{l'm'} j_{l'k} \rangle = \langle Y_{l''m''} j_{l''k} | \tilde{V}_1 | Y_{l'm'} j_{l'k} \rangle - \frac{2mk}{\hbar^2} \sum_l \sum_m \langle Y_{l''m''} j_{l''k} | \tilde{V}_1 | Y_{lm} j_{lk} \rangle \langle Y_{lm} h_{lk}^+ | V_1 | Y_{l'm'} j_{l'k} \rangle \quad (430)$$

This gives a set of linear, inhomogeneous algebraic equations which can be solved for $\langle Y_{l''m''} j_{l''k} | \tilde{V}_l | Y_{l'm'} j_{l'k} \rangle$. Next, we form $$\frac{2}{\pi} \sum_{l''m''} \sum_{l'm'} Y_{l''m''}(-\hat{k}) i^{-l''} Y_{l'm'}^*(\hat{k}) \langle Y_{l''m''} j_{l''k} | \tilde{V}_1 | Y_{l'm'} j_{l'k} \rangle = \quad (431)$$

$$\langle -\vec{k} | \tilde{V}_1 | \vec{k} \rangle$$

Then we can show that $$\tilde{V}_1(\vec{r}) = 2 \int d\vec{k}\, e^{-2i\vec{k}\cdot\vec{r}} \langle -\vec{k} | \tilde{V}_1 | \vec{k} \rangle \quad (432)$$

Now to generate $V_j(\vec{r})$, we form the following $$\langle -\vec{k} | \tilde{V}_j | \vec{k} \rangle = -\langle -\vec{k} | \tilde{V}_{j-1} \tilde{G}_{0k} \tilde{V}_1 | \vec{k} \rangle \quad (433)$$

$$-\langle -\vec{k} | \tilde{V}_{j-1} \tilde{G}_{0k} \tilde{V}_1 | \vec{k} \rangle = \quad (434)$$

$$-\int d\vec{r} \int d\vec{r}\,' e^{i\vec{k}\cdot\vec{r}} \tilde{V}_{j-1}(\vec{r}) \tilde{G}_{0k}(\vec{r}, \vec{r}\,') \tilde{V}_1(\vec{r}\,') e^{i\vec{k}\cdot\vec{r}\,'}$$

and we also form the following $$\tilde{V}_j(\vec{r}) = 2 \int d\vec{k}\, e^{-2i\vec{k}\cdot\vec{r}} \tilde{V}_j(2\vec{k}) \quad (435)$$

This gives a complete, absolutely convergent scheme, combined with a solution of a separable-kernel Fredholm equation of the second kind (inhomogeneous). All the mathematic proofs and derivations are rigorous.

One additional step can be to expand $V_1$ and $\tilde{V}_1$ in spherical harmonics as follows:

$$\tilde{V}_1(\vec{r}) = \sum_{\bar{l}\bar{m}} Y_{\bar{l}\bar{m}}(\hat{r}) \tilde{V}_1(\bar{l}\bar{m} | r) \quad (436)$$

$$\tilde{V}_1(\vec{r}) = \sum_{\bar{l}'\bar{m}'} Y_{\bar{l}'\bar{m}'}(\hat{r}) \tilde{V}_1(\bar{l}'\bar{m}' | r) \quad (437)$$

Now we can define $$C(l'm'\bar{l}\bar{m} | l''m'') = \int d\hat{r} Y_{l'm'}(\hat{r}) Y_{\bar{l}\bar{m}}(\hat{r}) Y_{l''m''}^*(\hat{r}) \quad (438)$$

and $$\tilde{V}_1(\bar{l}\bar{m} | l''l'k) = \int_0^\infty dr\, r^2 j_{l''}(kr) j_{l'}(kr) \tilde{V}_1(\bar{l}\bar{m} | r) \quad (439)$$

$$V_1(\bar{l}\bar{m} | l''l'k) = \int_0^\infty dr\, r^2 j_{l''}(kr) j_{l'}(kr) V_1(\bar{l}\bar{m} | r) \quad (440)$$

$$V_2(\bar{l}\bar{m} | l''l'k) = \int_0^\infty dr\, r^2 h_{l''}(kr) j_{l'}(kr) V_1(\bar{l}\bar{m} | r) \quad (441)$$

From these results, we get the following $$\sum_{\bar{l}m} C(l'm'\bar{l}\bar{m} | l''m'') V_1(\bar{l}\bar{m} | l''l'k) = \quad (442)$$

$$\sum_{\bar{l}m} C(l'm'\bar{l}\bar{m} | l''m'') \tilde{V}_1(\bar{l}\bar{m} | l''l'k) - \frac{2mk}{\hbar^2} \sum_{\bar{l}m} \sum_{l'''m'} \sum_{lm} C(lm\bar{l}\bar{m} | l''m'')$$

$$\tilde{V}_1(\bar{l}\bar{m} | l''lk) C(lm\bar{l}'\bar{m}' | l'm') V_2(\bar{l}'\bar{m}' | ll'k)$$

Then we want to solve for the elements $\tilde{V}_1(\bar{l}\bar{m} l''l'k)$, because there are fewer $\tilde{V}_1(\bar{l}\bar{m} l''l'k)$ elements to calculate than the matrix elements $\langle Y_{l''m''} j_{l''k} | \tilde{V}_l | Y_{l'm'} j_{l'k} \rangle$.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for analyzing inverse scattering spectral components comprising the steps of:
   irradiating an object with a measuring wave;
   measuring a reflection spectrum of the object;
   measuring a transmission spectrum of the object;
   calculating a transmission coefficient on a computer from:

$$t_k = 1 - \frac{ik}{2} \int_{-\infty}^{+\infty} dz\, e^{ikz} V(z) \psi_k^+(z),$$

where V(z) is the location interaction between the object and $\psi_k^+(z)$ is the measuring wave,
   calculating a reflection coefficient on the computer from:

$$r_k = -\frac{ik}{2} \int_{-\infty}^{-\infty} e^{-ikz} V(z) \psi_k^+(z)$$

using a set of definitions $$t_k \tilde{\psi}_k(z) = \psi_k^+(z)$$

$$\frac{r_k}{t_k} = \tilde{r}_k$$

$$\tilde{V}_1(z) = \int_{-\infty}^{+\infty} d(2k) \frac{2i}{k} \tilde{r}_k e^{-2ikz}$$

to convert a Lippmann-Schwinger inverse scattering equation $$\psi_k^+(z) = e^{ikz} - \frac{ik}{2}\int_{-\infty}^{+\infty} dz' e^{ik|z-z'|} V(z')\psi_k^+(z')$$

on the computer in a Volterra-type form $$\tilde{V}_1(z) = \int_{-\infty}^{+\infty} d(2k) e^{-2ikz} \frac{2i}{k} r_k \left[1 + \frac{ik\Delta}{2}\sum_j e^{-ikz_j} V(z_j)\tilde{\psi}_k(z)\right];$$

and iterating the Volterra-form of the Lippmann-Schwinger equation on the computer to produce an approximate solution $\tilde{V}_1(z)$, where $\tilde{V}_1(z)$ is absolutely and uniformly convergent.

2. The method of claim 1, wherein the approximate solution $\tilde{V}_1(z)$ includes four terms.

3. The method of claim 1, wherein the approximate solution $\tilde{V}_1(z)$ includes three terms.

4. The method of claim 1, wherein the approximate solution $\tilde{V}_1(z)$ includes two terms.

5. A method for analyzing inverse scattering components of a spectrum of an object of interest comprising the steps of:

obtaining a reflectance and/or transmission spectra of an object of interest using an incident waveform from the group consisting of an electromagnetic waveform, sonic waveform and mixtures or combinations thereof;

claculating a transmission coefficient on a computer from:

$$t_k = 1 - \frac{ik}{2}\int_{-\infty}^{+\infty} dz e^{ikz} V(z)\psi_k^+(z),$$

where V(z) is the location interaction between the object and $\psi_k^+(z)$ is the measuring wave, calculating a reflection coefficient on the computer from:

$$r_k = -\frac{ik}{2}\int_{-\infty}^{+\infty} e^{-ikz} V(z)\psi_k^+(z)$$

using a set of definitions $$t_k \tilde{\psi}_k(z) = \psi_k^+(z)$$

$$\frac{r_k}{t_k} = \tilde{r}_k$$

$$\tilde{V}_1(z) = \int_{-\infty}^{+\infty} d(2k) \frac{2i}{k} \tilde{r}_k e^{-2ikz}$$

to convert a Lippmann-Schwinger inverse scattering equation $$\psi_k^+(z) = e^{ikz} - \frac{ik}{2}\int_{-\infty}^{+\infty} dz' e^{ik|z-z'|} V(z')\psi_k^+(z')$$

on the computer into a Volterra-type form $$\tilde{V}_1(z) = \int_{-\infty}^{+\infty} d(2k) e^{-2ikz} \frac{2i}{k} r_k \left[1 + \frac{ik}{2}\int_{-\infty}^{+\infty} e^{-ikz} V(z_j)\tilde{\psi}_k(z)\right];$$

and iterating the Volterra-type form of the Lippmann-Schwinger equation on the computer to produce $\tilde{V}_1(z)$, where $\tilde{V}_1(z)$ is absolutely and uniformly convergent.

6. The method of claim 5, wherein the approximate solution $\tilde{V}_1(z)$ includes four terms.

7. The method of claim 5, wherein the approximate solution $\tilde{V}_1(z)$ includes three terms.

8. The method of claim 5, wherein the approximate solution $\tilde{V}_1(z)$ includes two terms.

9. An analytical instrument including an excitation source for producing an incident waveform, a detector for receiving either a transmission spectrum or a reflectance spectrum or both a transmission spectrum and a reflectance spectrum of an object or volume of interest, and a processing unit for analyzing the spectra, where the processing unit includes software encoding the inverse scattering method of claims 1, 2, 3, 4, 5, 6, 7, or 8.

10. A sonic analytical instrument including a sonic excitation source for producing an incident sonic waveform, a detector for receiving either a sonic transmission spectrum or a sonic reflectance spectrum or both a sonic transmission spectrum and a sonic reflectance spectrum of an object or volume of interest, and a processing unit for analyzing the sonic spectra, where the processing unit includes software encoding the inverse scattering method of claims 1, 2, 3, 4, 5, 6, 7, or 8.

11. An electromagnetic analytical instrument including an electromagnetic excitation source for producing an incident electromagnetic waveform, a detector for receiving either an electromagnetic transmission spectrum or an electromagnetic reflectance spectrum or both an electromagnetic transmission spectrum and an electromagnetic reflectance spectrum of an object or volume of interest, and a processing unit for analyzing the electromagnetic spectra, where the processing unit includes software encoding the inverse scattering method of claims 1, 2, 3, 4, 5, 6, 7, or 8.

12. An analytical instrument including a sonic excitation source and an electromagnetic excitation source for producing an incident sonic waveform and an incident electromagnetic waveform, a detector for receiving either a sonic transmission spectrum or a sonic reflectance spectrum or both a sonic transmission spectrum and a sonic reflectance spectrum of an object or volume of interest, a detector for receiving either an electromagnetic transmission spectrum or an electromagnetic reflectance spectrum or both an electromagnetic transmission spectrum and an electromagnetic reflectance spectrum of an object or volume of interest, and a processing unit for analyzing the sonic and electromagnetic spectra, where the processing unit includes software encoding the inverse scattering method of claims 1, 2, 3, 4, 5, 6, 7, or 8.

* * * * *